(12) United States Patent
Shin et al.

(10) Patent No.: US 9,381,168 B2
(45) Date of Patent: Jul. 5, 2016

(54) USE OF CAPSIATE OR DIHYDROCAPSIDATE

(75) Inventors: Dong Heun Shin, Seoul (KR); Young Guen Kwon, Seoul (KR); Bo Jeong Pyun, Seoul (KR); Tae-Yoon Kim, Seoul (KR)

(73) Assignee: Catholic University Industry Academy Cooperation Foundation, Seoul (KR)

( * ) Notice: Subject to any disclaimer, the term of this patent is extended or adjusted under 35 U.S.C. 154(b) by 435 days.

(21) Appl. No.: 12/742,245

(22) PCT Filed: May 27, 2008

(86) PCT No.: PCT/KR2008/002951
§ 371 (c)(1),
(2), (4) Date: Oct. 6, 2010

(87) PCT Pub. No.: WO2009/061051
PCT Pub. Date: May 14, 2009

(65) Prior Publication Data
US 2011/0028547 A1 Feb. 3, 2011

(30) Foreign Application Priority Data

Nov. 9, 2007 (KR) .................. 10-2007-0114135

(51) Int. Cl.
| | |
|---|---|
| *A61K 31/216* | (2006.01) |
| *A61P 17/00* | (2006.01) |
| *A61P 17/06* | (2006.01) |
| *A61K 31/04* | (2006.01) |
| *A61K 31/085* | (2006.01) |
| *A61K 31/222* | (2006.01) |
| *C07C 57/48* | (2006.01) |
| *C07C 57/46* | (2006.01) |

(52) U.S. Cl.
CPC .............. *A61K 31/04* (2013.01); *A61K 31/085* (2013.01); *A61K 31/222* (2013.01)

(58) Field of Classification Search
CPC .... A61K 31/04; A61K 31/085; A61K 31/222
USPC .................... 514/183, 549, 223, 228, 552
See application file for complete search history.

(56) References Cited

U.S. PATENT DOCUMENTS

| | | | | |
|---|---|---|---|---|
| 6,063,381 | A * | 5/2000 | Staggs ........................ | 424/734 |
| 2005/0271661 | A1 * | 12/2005 | Manivasakam et al. ... | 424/144.1 |
| 2006/0069102 | A1 * | 3/2006 | Leban et al. ............... | 514/253.1 |
| 2008/0182894 | A1 * | 7/2008 | Takino et al. ................ | 514/458 |

FOREIGN PATENT DOCUMENTS

WO    WO 2007013690 A1 *   2/2007

OTHER PUBLICATIONS

Bickers et. al. Journal of Investigative Dermatology 2006, 126, 2565-2575.*
Satyavan Singh, Robert Jarret, Vincent Russo, George Majetich, Joel Shimkus, Rodney Bushway, and Brian Perkins, Determination of Capsinoids by HPLC-DAD in Capsicum Species, J. Agric. Food Chem. 2009, 57, 3452-3457.*
Fulvio D'Acquisto, PhD, Michael J. May, PhD and Sankar Ghosh, PhD, Inhibition of Nuclear Factor Kappa B (NF- B): An Emerging Theme in Anti-Inflammatory Therapies, Feb. 2002 vol. 2 No. 1, 22-35.*
Alena Svobodová, Jitka Psotová, Daniela Walterová, Natural Phenolics in the Prevention of UV-Induced Skin Damage.A Review, Biomed. Papers 147(2), 137-145 (2003).*
Sancho R. et al., Eur. J. Immunol. vol. 32, 1753-1763, 2002.
Min, J-K et al., Cancer Research vol. 64, 644-651, 2004.
Macho A. et al., Eur. J. Nutr., vol. 42, 2-9, 2003.
Rosa A. et al., J. Agric. Food Chem., vol. 50, 7396-7401, 2002.
Yiu et al., "Interleukin 17-A inhibition in the treatment of psoriasis." Expert Review of Clinical Immunology, DOI: 10.1586/1744666X.2016X1112739. Nov. 2015 ISSN 1744-666X.
Lee et al., "Capsiate Inhibits DNFB-Induced Atopic Dermatitis in NC/Nga Mice through Mast Cell CD4+ T-Cell Inactivation." Journal of Investigative Dermatology, May 2015 vol. 135, 1977-1985.

* cited by examiner

*Primary Examiner* — Sarah Pihonak
*Assistant Examiner* — Jason A Deck
(74) *Attorney, Agent, or Firm* — Mintz Levin Cohn Ferris Glovsky and Popeo, P.C.; Kongsik Kim; Richard B. Emmons

(57) ABSTRACT

The present invention relates to a new use of capsiate or dihydrocapsiate, more particularly to a composition for preventing and treating inflammatory disease, angiogenesis-related disease and autoimmune disease or for suppressing immunity comprising capsiate, dihydrocapsiate or a pharmaceutically acceptable salt thereof as an effective ingredient. The composition and immunosuppressant of the present invention may be used for preventing and treating inflammatory disease, angiogenesis-related disease and autoimmune disease, and for suppressing immunity.

5 Claims, 15 Drawing Sheets

USE OF CAPSIATE OR DIHYDROCAPSIDATE

CROSS-REFERENCE TO RELATED APPLICATIONS

This application is a U.S. national phase application, pursuant to 35 U.S.C. §371 of PCT/KR2008/002951, filed May 27, 2008, designating the United States, which claims priority Korean Application No. 10-2007-004135,filed Nov. 9, 2007. The entire contents of the aforementioned patent applications are incorporated herein by this reference.

TECHNICAL FIELD

This application claims priority based on Korean Patent Application No. 2007-0114135, filed on Nov. 9, 2007, the entire contents of which are incorporated herein by reference.

The present invention relates to a new use of capsiate or dihydrocapsiate, more particularly to a composition for preventing and treating inflammatory disease, angiogenesis-related disease and autoimmune disease or for suppressing immunity comprising capsiate, dihydrocapsiate or a pharmaceutically acceptable salt thereof as an effective ingredient.

BACKGROUND ART

The compounds capsinoids include capsiate, dihydrocapsiate and nordihydrocapsiate. Especially, capsiate, which is mainly found in a nonpungent cultivar of red pepper, CH19 sweet, is known to provide effects comparable to those of capsaicin, including activation of the capsaicin receptor, suppression of body fat accumulation, and the like. Because capsiate is nonpungent, various researches are carried out on its mechanism. However, no concrete achievements have been made as yet.

Inflammatory response refers to the complex physiological response of vascular tissues to harmful stimuli, such as damages, bacteria, fungi, viruses, etc., including enzymatic activation caused by various inflammatory mediators and immunocytes, secretion of inflammatory mediators, infiltration of body fluid, cell migration, tissue destruction, or the like. As a result, such symptoms as erythema, edema, fever and pain are accompanied. Inflammatory response is a protective attempt by the organism to remove exogenous source of infection, regenerate damaged tissues and restore biological functions. However, excessive or prolonged inflammatory response, which may be caused by unremoved antigens or internal substances, can lead to damaged mucosa, tissue destruction, or such diseases as cancer, inflammatory skin disease, inflammatory bowel disease, arthritis, etc.

Until now, antihistaminic agents, vitamin ointments, and adrenocorticotropic hormones have been commonly used to treat inflammatory diseases. However, these drugs provide temporary effect only and sometimes are associated with severe side reactions. Accordingly, there is a need for the development of new substances effective in treating inflammatory diseases without side effects.

Angiogenesis is a process involving the growth of new blood vessels from pre-existing vessels. Angiogenesis is a normal process in embryonic development, as well as in wound healing and periodical changes in women's genital organs. However, uncontrolled angiogenesis may lead to pathological growth. Angiogenesis-related diseases include angioma, angiofibroma, vascular malformation and cardiovascular diseases such as arteriosclerosis, vascular adhesion, sclerotic edema and diabetes. Angiogenesis-related ophthalmologic diseases include corneal angiogenesis, neovascular glaucoma, diabetic retinopathy, angiogenesis-induced corneal disease, macular degeneration, pterygium, retinal degeneration, retrolental fibroplasia, trachoma, and the like. And angiogenesis-related diseases include chronic inflammatory diseases such as rheumatoid arthritis, eczematous diseases, telangiectasis, pyogenic granuloma, seborrheic dermatitis, psoriasis, contact dermatitis, atopic dermatitis and so on, and skin diseases such as acne. Angiogenesis is also a fundamental step in the growth and transition of tumors [*Opthalmol.* 102, 1261-1262, 1995; *J. Am. Acad. Derm.* 34(3):486-497, 1996; *Circulation* 93(4):632-682, 1996; *Cell* 86: 353-364, 1996].

The process of angiogenesis is composed of the steps: promotion of the growth of endothelial cells by tumor cytokine, vascular endothelial growth factor (VEGF) and basic fibroblast growth factor (bFGF); degradation of extracellular matrix proteins by matrix metalloproteinase (MMP); and migration of the endothelial cells mediated by membrane adhesion molecules, differentiation of the endothelial cells and formation of tube structures [Bussolino, F. et al., *Trends. Biochem. Sci.* 22:251-256, 1997; Kuwano, M. et al., *Intern. Med.* 40:565-572, 2001; Risau, W. Angiogenesis and endothelial cell function. *Arzneimittelforschung* 44:416-417, 1994].

Accordingly, the inhibition of the above steps has emerged as new therapeutic strategy for treating various angiogenesis-related diseases including cancers. Protease inhibitors, tyrosine kinase inhibitors, chemokines, interleukins and fragments of matrix proteins are developed as angiogenesis inhibitors [Abedi, H. et al., *J. Biol. Chem.* 272:15442-15451, 1997; Cao, Y., *Int. J. Biochem. Cell Biol.* 33:357-369, 2001; Fong, T. A. et al., *Cancer Res.* 59:99-106, 1999; Kwon, H. J. et al., *Acalycigorgia inermis. J. Microbiol. Biotechnol.* 11:656-662, 2001]. However, at present, few treatments are available which can effectively suppress angiogenesis and be used to treat angiogenesis-related diseases.

An immunosuppressant is a substance that performs immunosuppression of the immune system. They are mainly used to treat autoimmune diseases, and are largely classified into corticosteroid agents, cytotoxins, T cell signaling inhibitors, and the like.

When corticosteroids, which are steroid derivatives, bind to steroid receptors in the cytoplasm, and Hsp90 is dissociated from them, a complex of the drug and the receptor migrates into the nucleus, thereby exhibiting immunosuppressive effect. However, this drug is highly likely to remain in the body, and is reported to cause fatal results when administered for a long period of time, because it is highly likely to cause body weight increase, diabetes, loss of bone marrow, and adverse effects on reproductive function [Barnes P J, *Clin. Sci.* (Lond)., 94(6): 557-72. 1998; Boumpas D T et al., *Ann Intern Med.*, 119(12): 1198-208, 1993]. Cytotoxins interrupt gene (DNA) synthesis in dividing cells, thereby interrupting clonal expansion of T cells and suppressing immune response. Typical examples of the cytotoxins include azathioprine and cyclophosphoamide. It is reported that they may damage other differentiating cells [Aarbakke J, Janka-Schaub G, Elion G B., *Trends Pharmacol. Sci.*, 18(1): 3-7, 1997]. Further, they are known to induce severe adverse reactions, including reduced leucocytes and leukemia.

Accordingly, at present, T cell signaling inhibitors are hailed as immunosuppressants. The T cell signaling inhibitors exhibit immunosuppressive function by interrupting the signal pathway required for cell division. Cyclosporine A and FK506, which inhibit the production of interleukin-2 (IL-2) by interrupting the action of calcineurin, which is one of important molecules in immune response, are typical examples. In the course of studying the physiological functions of the capsinoids capsiate and dihydrocapsiate, the inventors of the present invention found out that they function to suppress inflammatory response, angiogenesis and immune response and completed the present invention by developing a composition for preventing or treating inflammatory disease or angiogenesis-related disease or for inhibiting immune response comprising capsiate or dihydrocapsiate.

DISCLOSURE

Technical Problem

Accordingly the present invention is directed to a new use of capsiate or dihydrocapsiate.

Technical Solution

In an aspect, the present invention provides a pharmaceutical composition for preventing and treating inflammatory disease comprising a capsinoid compound represented by the following Chemical Formula 1 or Chemical Formula 2, or a pharmaceutically acceptable salt thereof as an effective ingredient:

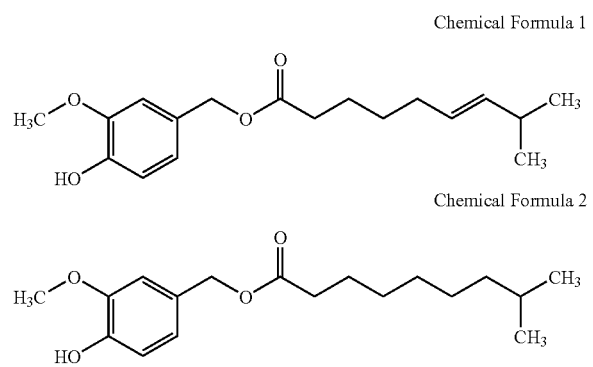

Chemical Formula 1

Chemical Formula 2

In another aspect, the present invention provides a composition for inhibiting angiogenesis comprising a capsinoid compound represented by Chemical Formula 1 or Chemical Formula 2, or a pharmaceutically acceptable salt thereof as an effective ingredient.

In another aspect, the present invention provides a pharmaceutical composition for preventing and treating angiogenesis-related disease comprising a capsinoid compound represented by Chemical Formula 1 or Chemical Formula 2, or a pharmaceutically acceptable salt thereof as an effective ingredient.

In another aspect, the present invention provides an immunosuppressant comprising a capsinoid compound represented by Chemical Formula 1 or Chemical Formula 2, or a pharmaceutically acceptable salt thereof as an effective ingredient.

In another aspect, the present invention provides a pharmaceutical composition for preventing and treating autoimmune disease comprising a capsinoid compound represented by Chemical Formula 1 or Chemical Formula 2, or a pharmaceutically acceptable salt thereof as an effective ingredient.

In another aspect, the present invention provides a use of a capsinoid compound represented by Chemical Formula 1 or Chemical Formula 2, or a pharmaceutically acceptable salt thereof for the preparation of a treating agent for inflammatory disease.

In another aspect, the present invention provides a method for preventing and treating inflammatory disease comprising administering a capsinoid compound represented by Chemical Formula 1 or Chemical Formula 2, or a pharmaceutically acceptable salt thereof to a subject in need thereof at an effective dose.

In another aspect, the present invention provides a use of a capsinoid compound represented by Chemical Formula 1 or Chemical Formula 2, or a pharmaceutically acceptable salt thereof for the preparation of a treating agent for angiogenesis-related disease.

In another aspect, the present invention provides a method for preventing and treating angiogenesis-related disease comprising administering a capsinoid compound represented by Chemical Formula 1 or Chemical Formula 2, or a pharmaceutically acceptable salt thereof to a subject in need thereof at an effective dose.

In another aspect, the present invention provides a use of a capsinoid compound represented by Chemical Formula 1 or Chemical Formula 2, or a pharmaceutically acceptable salt thereof for the preparation of an immunosuppressant.

In another aspect, the present invention provides a method for preventing and treating autoimmune disease comprising administering a capsinoid compound represented by Chemical Formula 1 or Chemical Formula 2, or a pharmaceutically acceptable salt thereof to a subject in need thereof at an effective dose.

Hereinafter, the present invention will described in more detail.

The present invention provides a composition comprising a capsinoid compound represented by the following Chemical Formula 1 or Chemical Formula 2 or a pharmaceutically acceptable salt thereof as an effective ingredient:

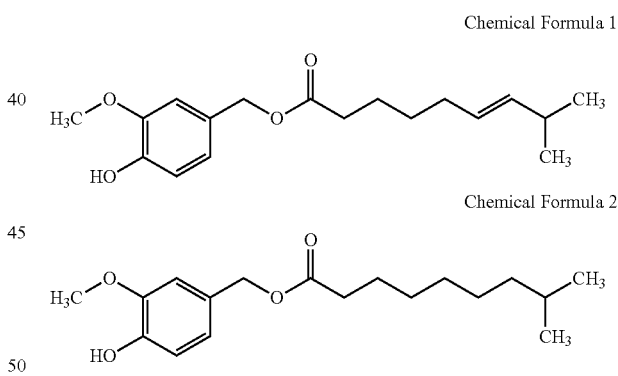

Chemical Formula 1

Chemical Formula 2

The capsinoid compound represented by Chemical Formula 1 is capsiate, and the capsinoid compound represented by Chemical Formula 2 is dihydrocapsiate. These capsinoid compounds may be isolated and purified from natural product, purchased commercially, or synthesized chemically by a method known in the related art.

Preferably, capsiate or dihydrocapsiate may be isolated and purified from natural product. More preferably; it may be isolated and purified from CH19 sweet, a nonpungent cultivar of red pepper. Capsiate or dihydrocapsiate may be extracted by a method commonly used in the related art, including organic solvent extraction and chromatography.

In an example that follows, the effect of capsiate and dihydrocapsiate on the inhibition of reactive oxygen species (ROS) generation in cells irradiated with UV was investigated. As a result, treatment with capsiate or dihydrocapsiate resulted in decreased ROS. Thus, it was confirmed that capsiate and dihydrocapsiate provide antioxidative effect (see Example 1).

In another example that follows, the effect of capsiate and dihydrocapsiate on the inhibition of UV-induced COX-2 expression, UV-induced expression of pro-inflammatory cytokines IL-6, IL-8 and tumor necrosis factor-α (TNF-α), and UV-induced expression of angiogenesis factors VEGF, MMP-2 and MMP-9 was investigated. As a result, capsiate or dihydrocapsiate inhibited UV-induced COX-2 expression, UV-induced expression of pro-inflammatory cytokines IL-6, IL-8 and TNF-α, and UV-induced expression of angiogenesis factors VEGF, MMP-2 and MMP-9. Thus, it was confirmed that capsiate or dihydrocapsiate provides the effect of inhibiting UV-induced inflammatory response and angiogenesis resulting therefrom (see Examples 2-4).

In another example that follows, the effect of capsiate on the inhibition of UV-induced inflammatory response and skin damage, UV-induced COX-2 expression, UV-induced expression of pro-inflammatory cytokines IL-6 and TNF-α, UV-induced expression of angiogenesis factors Ki67, platelet/endothelial cell adhesion molecule-1 (PECAM-1), intercellular cell adhesion molecule-1 (ICAM-1), VEGF, MMP-2 and MMP-9 and UV-induced erythema was investigated using an animal model. As a result, capsiate mitigated UV-induced inflammatory response, skin damage and erythema, and inhibited expression of COX-2, pro-inflammatory cytokines IL-6 and TNF-α and angiogenesis factors Ki67, PECAM-1, ICAM-1, VEGF, MMP-2 and MMP-9. Thus, it was confirmed that capsiate has the effect of inhibiting UV-induced inflammatory response and angiogenesis resulting therefrom in vivo (see Examples 5-8).

Accordingly, the present invention provides a pharmaceutical composition for preventing and treating inflammatory disease comprising capsiate, dihydrocapsiate or a pharmaceutically acceptable salt thereof.

In the present invention, capsiate or dihydrocapsiate may be used in itself or in the form of a pharmaceutically acceptable salt. As used herein, "pharmaceutically acceptable" means what is physiologically acceptable and generally does not cause allergic responses or other similar reactions when administered to humans. Preferably, the salt may be an acid addition salt formed from a pharmaceutically acceptable free acid. The free acid may be either an organic acid or an inorganic acid. The organic acid may be citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid or aspartic acid, but not limited thereto. And, the inorganic acid may be hydrochloric acid, bromic acid, sulfuric acid or phosphoric acid, but not limited thereto.

The inflammatory diseases to which the compound of the present invention can be applied may include inflammatory skin disease, inflammatory bowel disease such as Crohn's disease, ulcerative colitis, peritonitis, osteomyelitis, phlegmon, meningitis, encephalitis, pancreatitis, trauma-induced shock, bronchial asthma, allergic rhinitis, cystic fibrosis, stroke, acute bronchitis, chronic bronchitis, acute bronchiolitis, chronic bronchiolitis, osteoarthritis, gout, spondyloarthropathy, ankylosing spondylitis, Reiter's syndrome, psoriatic arthropathy, enteropathic spondylitis, juvenile arthropathy, juvenile ankylosing spondylitis, reactive arthropathy, inflammatory arthritis, post-inflammatory arthritis, gonococcal arthritis, tuberculous arthritis, viral arthritis, mycotic arthritis, syphilitic arthritis, Lyme disease, vasculitic syndrome-related arthritis, polyarteritis nodosa, hypersensitivity vasculitis, Luegenec's granulomatosis, rheumatoid polymyalgia, articular cell arteritis, calcium crystal deposition arthropathy, pseudogout, nonarticular rheumatism, bursitis, tenosynovitis, epicondylitis (tennis elbow), neuropathic joint disease (Charco and joint), hemarthrosis, Henoch-Schönlein purpura, hypertrophic osteoarthropathy, multicentric reticulohistiocytoma, surcoilosis, hemochromatosis, sickle-cell anemia and other hemoglobinopathies, hyperlipoproteinemia, hypogammaglobulinemia, familial Mediterranean fever, Behçet disease, systemic lupus erythematosus, recurrent fever, psoriasis, multiple sclerosis, septicemia, septic shock, multiple organ dysfunction syndrome, acute respiratory distress syndrome, chronic obstructive pulmonary disease, acute lung injury, bronchopulmonary dysplasia, and the like, but not limited thereto.

Further, the inflammatory skin disease may include skin inflammation, acute/chronic eczema, contact dermatitis, atopic dermatitis, seborrheic dermatitis, lichen simplex chronicus, intertrigo, exfoliative dermatitis, papular urticaria, psoriasis, psoriasisarthritis, solar dermatitis, sunburn, acne, and the like, but not limited thereto.

A pharmaceutical composition of the present invention may comprise capsiate, dihydrocapsiate or a pharmaceutically acceptable salt thereof alone or together with pharmaceutically acceptable carrier or diluent.

A pharmaceutically acceptable carrier, for example, carriers for the parenteral or oral preparations may be included. The carriers for the oral preparations may comprise lactose, starch, cellulose derivatives, magnesium stearate, stearic acid. In addition, the carriers for the parenteral preparations may comprise water, oil, saline, aqueous glucose and glycol, and stabilizers and preservatives. The examples of the stabilizers may be antioxidant such as sodium hydrogen sulfite, sodium sulfite, and ascorbic acid. The examples of the preservatives may be benzalkonium chloride, methyl- or prophyl-paraben, and chlorobutanol. The list of pharmaceutically acceptable carriers are disclosed in Remington's Pharmaceutical Sciences, 19th ed., Mack Publishing Company, Easton, Pa., 1995.

A pharmaceutical composition for preventing and treating inflammatory disease of the present invention may be administered to mammals including human beings by any routes. For example, it may be administered parenterally or orally. For parenteral administration, but not limited thereto, it may be administered parenterally, by intravenous, intramuscular, intraarterial, intramarrow, subdural, intracardiac, intracutaneous, subcutaneous, intraperitoneal, intranasal, gastrointestinal tracts, parenteral, sublingual or rectum. Preferably, a pharmaceutical composition of the present invention may be administered by intracutaneous. The said 'intracutaneous' refers to transfer effective amount of an active ingredient which is comprised in the composition for preventing and treating inflammatory disease by administered a pharmaceutical composition of the present invention into the cell or the skin. For example, an injectable form of the pharmaceutical composition of the present invention may be administered by lightly pricking the skin with 30-gauge injection needle, or applying directly into the skin.

A pharmaceutical composition of the present invention may be prepared in the form of oral preparation or parenteral preparation according to the described above.

In case of the formulation for oral administration, the composition of the present invention may be formulated into powders, granules, tablets, pills, and sugar-coated tablets, capsules, liquids, gels, syrups, slurrys, and emulsions by using the method known in the art. For example, preparations for oral administration may be harvested in the form of tablets or sugar-coated tablets by mixing an effective component with a solid excipient, grinding, and adding appropriate supplemental agents, then manufacturing a form of granular mixture. For examples of appropriate excipient, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as an solutionizer. Further, the inventive pharmaceutical composition may comprise anti-coaglutinating agent, lubricant, wetting agents, flavors, emulsifying agents and antiseptics additionally.

In case of pharmaceutical formulations for parenteral administration, it may be prepared in the forms of injectable preparations, creams, lotions, ointments, oils, humectant, gels, aerosol, and nausal inhalations by the method well known in the art. The formulation of the above-mentioned is well described in Remington's Pharmaceutical Science, 15th Edition, 1975, Mack Publishing Company, Easton, Pa. 18042, Chapter 87: Blaug, Seymour.

Total effective amount of capsiate or dihydrocapsiate of the present invention may be administered to a patient with a single dose, or may be administered with multiple doses by fractionated treatment protocol. The pharmaceutical compositions of the present invention may contain variable amount of effective ingredient according to the disease severity. In case of parenteral administration, the effective amount of capsiate or dihydrocapsiate of the present invention is preferably about 0.01 ug to 1,000 mg/kg body weight/day, most preferably 0.1 ug to 100 mg/kg body weight/day. However, the dose of the said capsiate or dihydrocapsiate may be suitably determined by considering various factors, such as age, body weight, health condition, sex, disease severity, diet and excretion of a subject in need of treatment, as well as administration time and administration route. Therefore, when those are considered, skilled person in the art may determine appropriate dose of the said capsiate or dihydrocapsiate for a centain use for preparing reagent for preventing and treating inflammatory disease. A pharmaceutical composition of the present invention may not limit formulations, administration routes, and administration methods as long as they show the effect of the present invention.

In another example that follows, the effect of capsiate or dihydrocapsiate on proliferation of endothelial cells induced by the angiogenesis factor VEGF was investigated. As a result, capsiate and dihydrocapsiate have the effect of inhibiting the proliferation of endothelial cells, which was confirmed not due to cell toxicity (see Example 9).

In another example that follows, the mechanism by which the proliferation of endothelial cells is inhibited was identified through the analysis of change of cell cycle and expression of cyclins. As a result, it was confirmed that capsiate and dihydrocapsiate inhibits the progress of cell cycle from $G_1$ phase to S phase by reducing the expression of cyclin D1 (see Example 10).

In another example that follows, the effect on migration of endothelial cells and tube formation induced by VEGF was investigated. As a result, treatment with VEGF resulted in increased chemotactic mobility and tube formation, whereas treatment with capsiate or dihydrocapsiate resulted in decrease thereof (see Example 11).

In another example that follows, the effect on change of endothelial permeability and expression of VE-cadherin induced by VEGF, was investigated. As a result, it was confirmed that capsiate and dihydrocapsiate inhibit tyrosine phosphorylation of VE-cadherin, thereby lowering the epithelial permeability induced by VEGF (see Example 12).

In another example that follows, the effect on angiogenesis of endothelial cells induced by VEGF was investigated. As a result, it was confirmed that capsiate and dihydrocapsiate inhibit sprouting of the aortic ring, angiogenesis in Matrigel plug and production of endothelial cells, thereby inhibiting VEGF-induced angiogenesis (see Example 13).

Accordingly, the present invention provides a composition for inhibiting angiogenesis comprising capsiate, dihydrocapsiate or a pharmaceutically acceptable salt thereof as an effective ingredient.

Further, the present invention provides a pharmaceutical composition for preventing and treating angiogenesis-related disease comprising capsiate, dihydrocapsiate or a pharmaceutically acceptable salt thereof as an effective ingredient.

The angiogenesis-related disease may include cancer, diabetes, rheumatoid arthritis, arteriosclerosis, angioma, hemangiofibroma, diabetic retinopathy, retinopathy of prematurity, neovascular glaucoma, angiogenesis-induced corneal disease, macular degradation, macular degeneration, pterygium, retinal degeneration, retrolental fibroplasia, trachoma, telangiectasis, pyogenic granuloma, psoriasis and acne. Further, the cancer may include colon cancer, lung cancer, liver cancer, stomach cancer, esophageal cancer, pancreatic cancer, gallbladder cancer, renal cancer, bladder cancer, prostatic cancer, testicular cancer, cervical cancer, endometrial cancer, choriocarcinoma, ovarian cancer, breast cancer, thyroid cancer, brain cancer, head and neck cancer, malignant melanoma, Kaposi's sarcoma, skin cancer, lymphoma and aplastic anemia.

In another example that follows, T cells were treated with capsiate. As a result, proliferation of T cells was markedly inhibited, production of IL-2 by T cells decreased significantly, and tyrosine phosphorylation in T cells was suppressed. Particularly, it was confirmed that capsiate can inhibit the proliferation and activation of T cells by suppressing phosphorylation by Lck (see Example 14).

Accordingly, the present invention provides an immunosuppressant comprising capsiate, dihydrocapsiate or a pharmaceutically acceptable salt thereof as an effective ingredient.

The immunosuppressant of the present invention can suppress tyrosine phosphorylation in T cells, particularly phosphorylation by Lck. Therefore, it can be a useful immunosuppressant for inhibiting the proliferation and activation of T cells.

Further, the present invention provides pharmaceutical composition for preventing and treating autoimmune disease comprising capsiate, dihydrocapsiate or a pharmaceutically acceptable salt thereof as an effective ingredient.

The pharmaceutical composition for preventing and treating autoimmune disease of the present invention may be useful in preventing or treating autoimmune disease by remarkably reducing the production of IL-2 by T cells.

The autoimmune disease refers to a non-malignant disease or disorder arising from and directed against an individual's own tissues. Preferably, the autoimmune disease may be a disease selected from a group consisting of rheumatoid arthritis, lupus erythematosus, multiple sclerosis and uveitis, but not limited thereto.

A pharmaceutical composition for suppressing immunity and preventing and treating inflammatory disease of the present invention may not limit formulations, administration routes, and administration methods as long as they show the effect of the present invention.

To achieve the above objects, the present invention provides use of a capsinoid compound represented by the following Chemical Formula 1 or Chemical Formula 2, or a pharmaceutically acceptable salt thereof for the preparation of a treatment agent for treating inflammatory disease.

To achieve another objects, the present invention provides a method for preventing and treating inflammatory disease comprising administering a capsinoid compound represented by Chemical Formula 1 or Chemical Formula 2, or a pharmaceutically acceptable salt thereof to a subject in need thereof at an effective dose.

In addition, the present invention provides a use of a capsinoid compound represented by Chemical Formula 1 or 2 or a pharmaceutically acceptable salt thereof for the preparation of a treatment agent for angiogenesis-related disease.

In addition, the present invention provides a method for preventing and treating angiogenesis-related disease comprising administering a capsinoid compound represented by Chemical Formula 1 or Chemical Formula 2, or a pharmaceutically acceptable salt thereof to a subject in need thereof at an effective dose.

In addition, the present invention provides a use of a capsinoid compound represented by Chemical Formula 1 or Chemical Formula 2, or a pharmaceutically acceptable salt thereof for the preparation of an immunosuppressant.

In addition, the present invention provides a method for preventing and treating autoimmune disease comprising administering a capsinoid compound represented by Chemical Formula 1 or 2 or a pharmaceutically acceptable salt thereof to a subject in need thereof at an effective dose.

As used herein, the "subject in need" refers to a mammal in need of preventing and treating inflammatory disease, angiogenesis-related disease and autoimmune disease, and, preferably, it refers to a human.

As used herein, the "effective amount" may be administered to a patient with a single dose, or may be administered with multiple doses by fractionated treatment protocol. The pharmaceutical compositions of the present invention may contain variable amount of effective ingredient according to the disease severity. In case of parenteral administration, the effective amount of capsiate or dihydrocapsiate of the present invention is preferably about 0.01 ug to 1,000 mg/kg body weight/day, most preferably 0.1 ug to 100 mg/kg body weight/day. However, the dose of the said capsiate or dihydrocapsiate may be suitably determined by considering various factors, such as age, body weight, health condition, sex, disease severity, diet and excretion of a subject in need of treatment, as well as administration time and administration route. Therefore, when those are considered, skilled person in the art may determine appropriate dose of the said capsiate or dihydrocapsiate for a centain use for preparing reagent for preventing and treating inflammatory disease. A pharmaceutical composition of the present invention may not limit formulations, administration routes, and administration methods as long as they show the effect of the present invention.

Advantageous Effects

Accordingly, the present invention provides a composition for preventing and treating inflammatory disease, angiogenesis-related disease and autoimmune disease or immunosuppressant comprising capsiate, dihydrocapsiate or a pharmaceutically acceptable salt thereof as an effective ingredient. The composition and immunosuppressant of the present invention may be used for preventing and treating inflammatory disease, angiogenesis-related disease or autoimmune disease, or for inhibiting immune response.

MODE FOR INVENTION

Hereinafter, the present invention will be descried in detail through examples.

However, the following examples are for illustrative purposes only, and the present invention is not limited by the following examples.

Example 1

Inhibition Effect on Production of Intracellular Reactive Oxygen Species (ROS) Induced by UV Irradiation 1-1. Inhibition Effect of Capsiate on Production of Intracellular ROS $5 \times 10^5$ HaCaT cells (acquired from Professor N. Fusenig of the German Cancer Research Center), which are a human keratinocyte cell line, were placed on a 60 mm Petri dish ($1 \times 10^6$ cells for a 100 mm Petri dish) and cultured for 24 hours in Dulbecco's modified Eagle's medium (DMEM) containing 10% fetal bovine serum (FBS).

After treating with 50 μM capsiate for 30 minutes, the cells were washed 3 times with phosphate buffered saline (PBS). In order to induce the production of ROS, UV was irradiated at an intensity of 100 J/m$^2$, using a UV lamp (FSX 24 T12/UVB/HO, Pansol™ USA). Immediately after the UV irradiation, the cells were washed again with PBS and further cultured for 2 hours in DMEM containing 1% FBS, which was treated with capsiate at the same concentration as in the pre-treatment. After treating with 25 μM 2,7-dichlorofliuorescin diacetate (DCFH-DA) in Hank's balanced salt solution (HBSS, BioWhittaker Cambrex, USA) for 30 minutes, the cells were washed 3 times with PBS.

Figure 1:
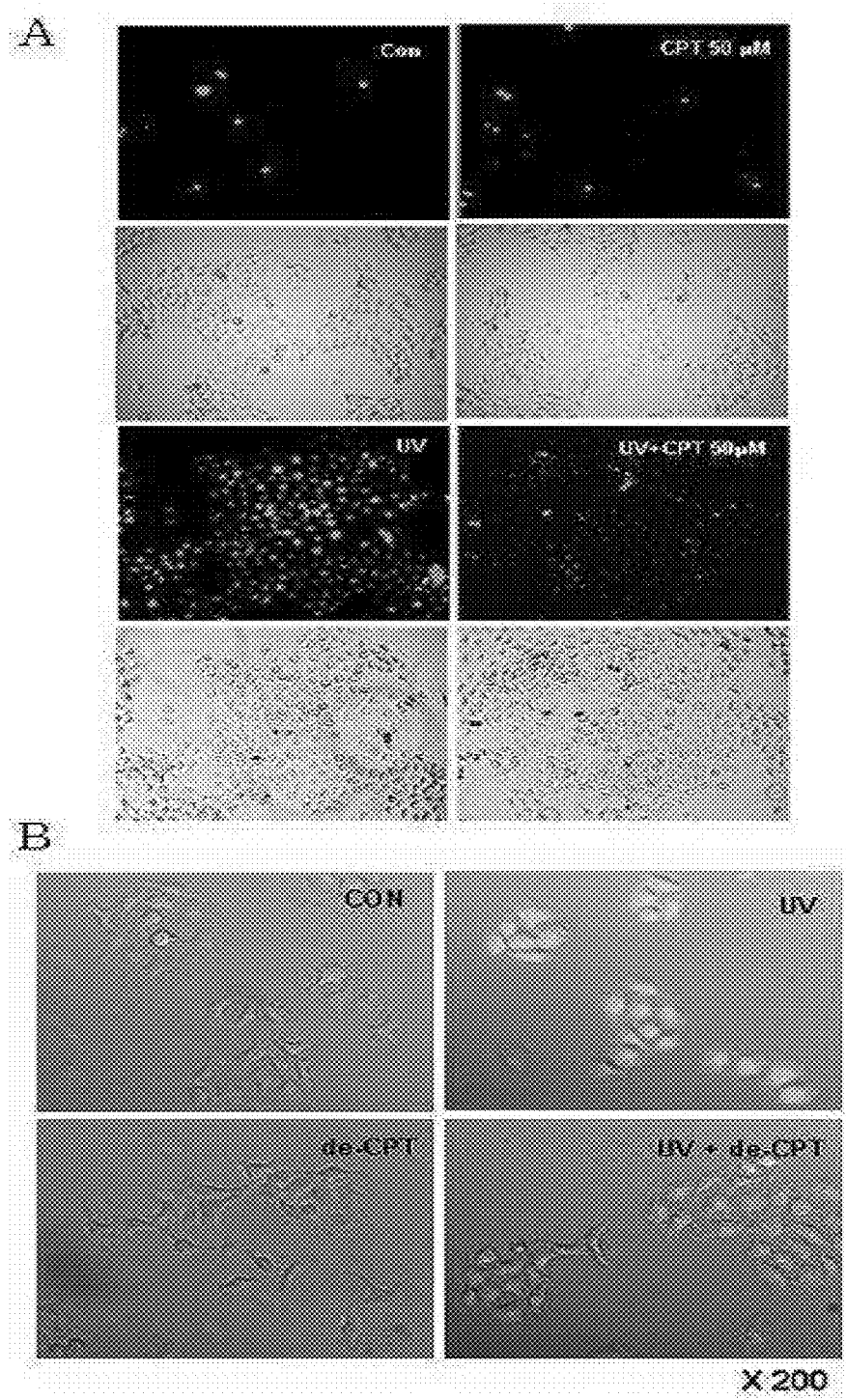
FIG. 1 shows the effect of suppressing reactive oxygen species in cells of capsiate (A) and dihydrocapsiate (B) (Con: non-treated group; CAT, deCPT: test group A; UV: control group; UV+CAT, UV+deCPT: test group B; CAT: capsiate; deCPT: dihydrocapsiate).

The treated cells were observed under a fluorescence microscope (Carl Zeiss, USA) in order to measure the ROS produced by the UV irradiation. Test groups were as follows: non-treated group—treated with neither UV nor capsiate; test group A—treated only with capsiate; control group—treated only with UV; test group B—treated with UV and capsiate (in Examples 1-4). As a result, as shown in FIG. 1A, when capsiate was treated before UV irradiation (test group B), the production of intracellular ROS decreased remarkably as compared to when only UV was irradiated (control group). Thus, it was confirmed, that capsiate is effective in suppressing the production of ROS induced by UV. Accordingly, capsiate is deemed to have antioxidative effect.

1-2. Inhibition Effect of Dihydrocapsiate on Production of Intracellular ROS

Inhibition effect on the production of intracellular ROS induced by UV was measured in the same manner as Example 1-1, except for using dihydrocapsiate instead of capsiate.

As a result, as shown in FIG. 1B, when dihydrocapsiate was treated before UV irradiation (test group B), the production of intracellular ROS decreased remarkably as compared to when only UV was irradiated (control group). Thus, it was confirmed that dihydrocapsiate is effective in suppressing the production of ROS induced by UV. Accordingly, dihydrocapsiate is deemed to have antioxidative effect.

Example 2

Inhibition Effect on UV-Induced COX-2 Expression 2-1. Inhibition Effect of Capsiate on UV-Induced COX-2 Expression In order to investigate the effect of capsiate on UV-induced COX-2 expression in human keratinocytes, 5×10$^5$ HaCaT cells were placed on a 60 mm Petri dish and cultured for 24 hours in DMEM containing 10% FBS.

Subsequently, the cells were cultured for 24 hours in DMEM containing 1% FBS until starvation. Then, after treating with capsiate for 30 minutes at different concentrations (10 μM, 25 μM, 50 μM), followed by washing 3 times with PBS, UV was irradiated at an intensity of 100 J/m$^2$ in order to induce the expression of COX-2. Immediately after the UV irradiation, the cells were washed again with PBS and further cultured for 16 hours in DMEM containing 1% FBS, which was treated with capsiate at the same concentration as in the pre-treatment.

Western blotting was carried out as follows in order to evaluate the degree of COX-2 expression in the cells. Cells of each test group were lysed using RIPA buffer containing 2 mM EDTA, 137 mM NaCl, 20 mM Tris-HCl (pH 8.0), 1 mM sodium vanadate, 10 mM NaF, 1 mM PMSF (phenylmethane-sulfonyl fluoride), 1% Triton X-100, 10% glycerol and protease inhibitor cocktail, and proteins were isolated by SDS-PAGE using 10% acrylamide gel. After transferring to nylon membrane, wanted proteins were isolated using goat anti-COX-2 antibody (Santa Cruz, USA) and anti-goat IgG-horse radish peroxidase (HRP) conjugation antibody (1; 10,000, Zymed) as the secondary antibody. Detection was made using ECL (Amersham, USA), followed by imaging using RAS 3000 imaging system (Fuji Film, Japan).

Figure 2:
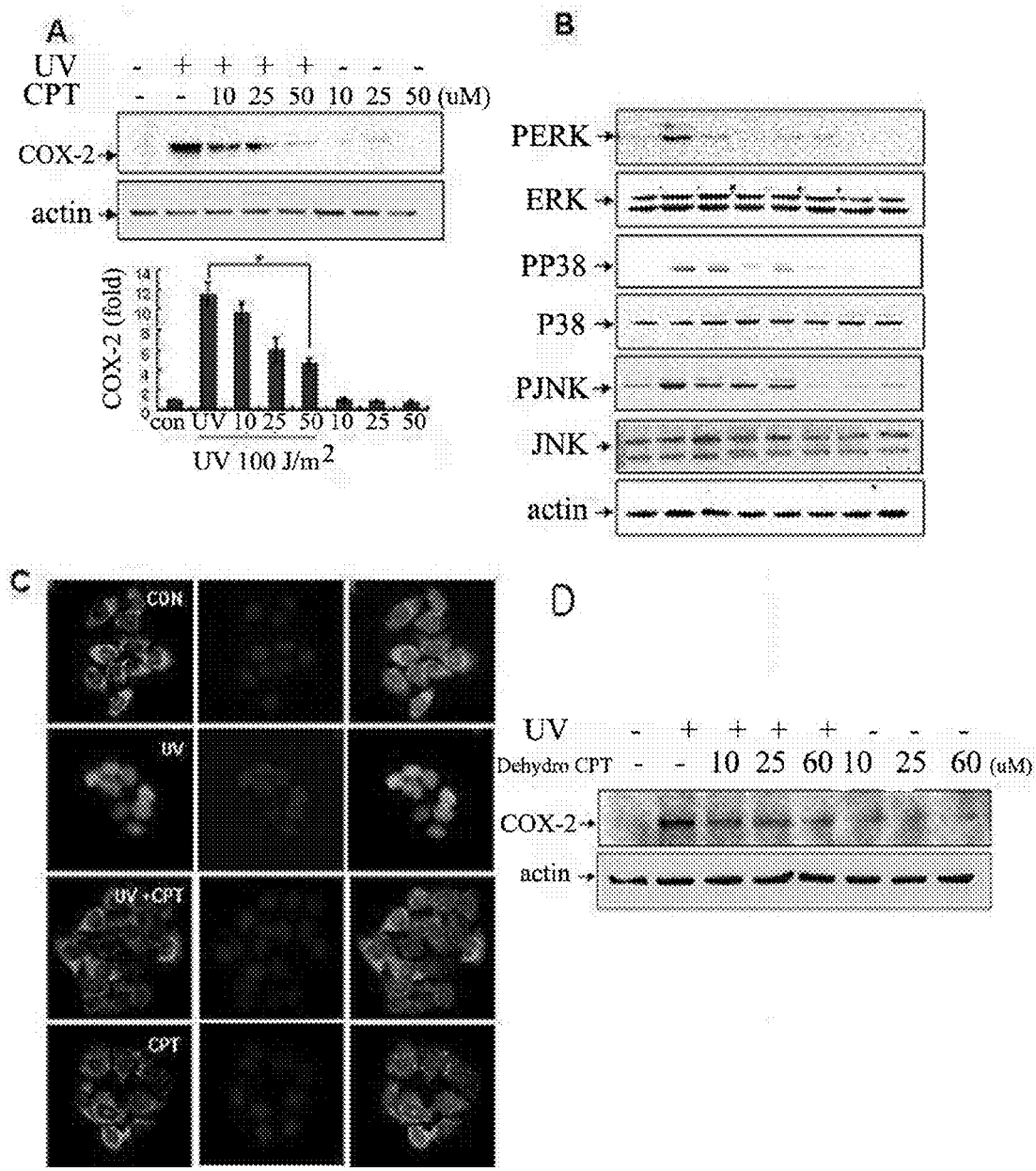
FIG. 2 shows the effect of suppressing COX-2 expression of capsiate (A) and dihydrocapsiate (D) and the effect on MAPK (B) and NF-κB (C) signaling (PERK: phosphorylated ERK, PP38: phosphorylated P38).

As a result, as shown in FIG. 2A, COX-2 expression increased due to the UV irradiation in the control group. When capsiate was treated, the increased COX-2 expression decreased in a concentration-dependent manner.

2-2. Identification of COX-2 Expression Inhibition Mechanism

Signaling of MAPKs and the transcription factor NF-κB was investigated in order to identify how capsiate inhibits the COX-2 expression in human keratinocytes induced by UV irradiation.

MAPKs are involved in inflammatory response, apoptosis and carcinogenesis. They are also involved in cell damage induced by UV irradiation [Peus D, Vasa R A, Beyerle A, Meves A, Krautmacher C, Pittelkow M R. UVB activates ERK1/2 and p38 signaling pathways via reactive oxygen species in cultured keratinocytes. *J. Invest. Dermatol.* 1999; 112:7516]. And, the transcription factor NF-κB regulates various cellular factors expressed in relation to inflammatory response, including COX-2 [Paik J, Lee J Y, Hwang D. Signaling pathways for TNFα-induced COX-2 expression: mediation through MAP kinases and NFκB, and inhibition by certain nonsteroidal anti-inflammatory drugs. *Adv. Exp. Med. Biol.* 2002; 507: 503-508.].

Western blotting was performed in the same manner as in Example 2-1 in order to identify the factor that affects the COX-2 expression regulated by capsiate, except for treating the cells with capsiate at different concentrations (10 μM, 25 μM and 50 μM) prior to UV irradiation, and using rabbit anti-ERK antibody, rabbit anti-p-ERK antibody, rabbit anti-p38 antibody, rabbit anti-p-p38 antibody, rabbit anti-JNK antibody and rabbit anti-p-JNK antibody (cell signaling), and anti-rabbit IgG-HRP conjugation antibody (Zymed) as the secondary antibody, 30 minutes after UV irradiation.

As a result, as shown in FIG. 2B, no particular change was observed for p38 and JNK, but the phosphorylation of ERK was inhibited by capsiate.

2-3. Identification of COX-2 Expression Inhibition Mechanism

In order to investigate whether the transcription factor NF-κB is activated, the human keratinocyte cell line HaCaT cells were stained by immunohistochemical staining as follows.

The cells were placed on a 14 mm culture slide and cultured for 24 hours in DMEM containing 10% FBS. Subsequently, the cells were cultured for 24 hours in DMEM containing 1% FBS until starvation. Then, after treating with 25 μM capsiate for 30 minutes, followed by washing 3 times with PBS, UV was irradiated at an intensity of 100 J/m$^2$. Immediately after the UV irradiation, the cells were washed again with PBS and further cultured for 4 hours in DMEM containing 1% FBS, which was treated with capsiate at the same concentration as in the pre-treatment. The cells were fixed for 5 minutes using methanol for immunohistochemical staining.

The fixed cells were blocked using 10% normal goat serum and washed 3 times with PBS. After fluorescence staining NF-κB using rabbit anti-NF-κB antibody (Santa Cruz, USA) and Alexa 488-labeled anti-rabbit IgG secondary antibody (Invitrogen, USA), counter staining was carried out using Hoechst (Sigma, St. Louis, Mo.).

As a result, as shown in FIG. 2C, NF-κB was activated by the UV irradiation and migrated into the nuclei. In contrast, in the test group B, which was treated with capsiate prior to the UV irradiation, NF-κB existed in the cytoplasm like the non-treated group or the test group A, which was treated only with capsiate. Accordingly, it was confirmed that capsiate inhibits the UV-induced migration of NF-κB into the nuclei.

2-4. Inhibition Effect of Dihydrocapsiate on UV-Induced COX-2 Expression

In order to investigate the effect of dihydrocapsiate on UV-induced COX-2 expression in human keratinocytes, the degree of COX-2 expression was evaluated in the same manner as Example 2-1, except for using dihydrocapsiate instead of capsiate.

As a result, as shown in FIG. 2D, COX-2 expression increased in the control group due to UV irradiation. Treatment with dihydrocapsiate resulted in the decrease of the increased COX-2 expression in a concentration-dependent manner.

Example 3

Inhibition Effect of Capsiate on UV-Induced Increase of Pro-Inflammatory Cytokines UV irradiation results in the increase of cytokines such as IL-6, IL-8 and TNF-α in the skin tissue, which mediate inflammatory responses. In order to investigate the effect of capsiate on this action, experiment was carried out as follows using a human keratinocyte cell line.

$1 \times 10^6$ HaCaT cells were placed on a 100 mm Petri dish and cultured for 24 hours in DMEM containing 10% FBS. Subsequently, the cells were cultured for 24 hours in DMEM containing 1% FBS until starvation. Then, after treating with capsiate at different concentrations (10 μM, 25 μM, 50 μM) for 30 minutes, followed by washing 3 times with PBS, UV was irradiated at an intensity of 100 $J/m^2$ to induce the production of cytokines. Immediately after the UV irradiation, the cells were washed again with PBS and further cultured for 4 hours in DMEM containing 1% FBS, which was treated with capsiate at the same concentration as in the pre-treatment.

Then, the degree of mRNA expression for IL-6, IL-8 and TNF-α induced mainly in the skin by the UV irradiation was evaluated by RT-PCR in order to measure the inhibition effect against the pro-inflammatory cytokines.

RNAs were extracted from the cells of each test group using Trizol (Invitrogen, USA) and used as template for PCR (PTC-225 Peltier thermal cycler, MJ Research, USA) to prepare cDNAs for each test group. Using the resultant cDNAs as template, the degree of mRNA expression for IL-6, IL-8 and TNF-α was measured by RT-PCR (Roter Gene 6000 series, Corbett Research, Australia) using commercial IL-6, IL-8 and TNF-α primers. The degree of mRNA expression for the intracellular pro-inflammatory cytokines was compared with that of the non-treated group.

Figure 3:
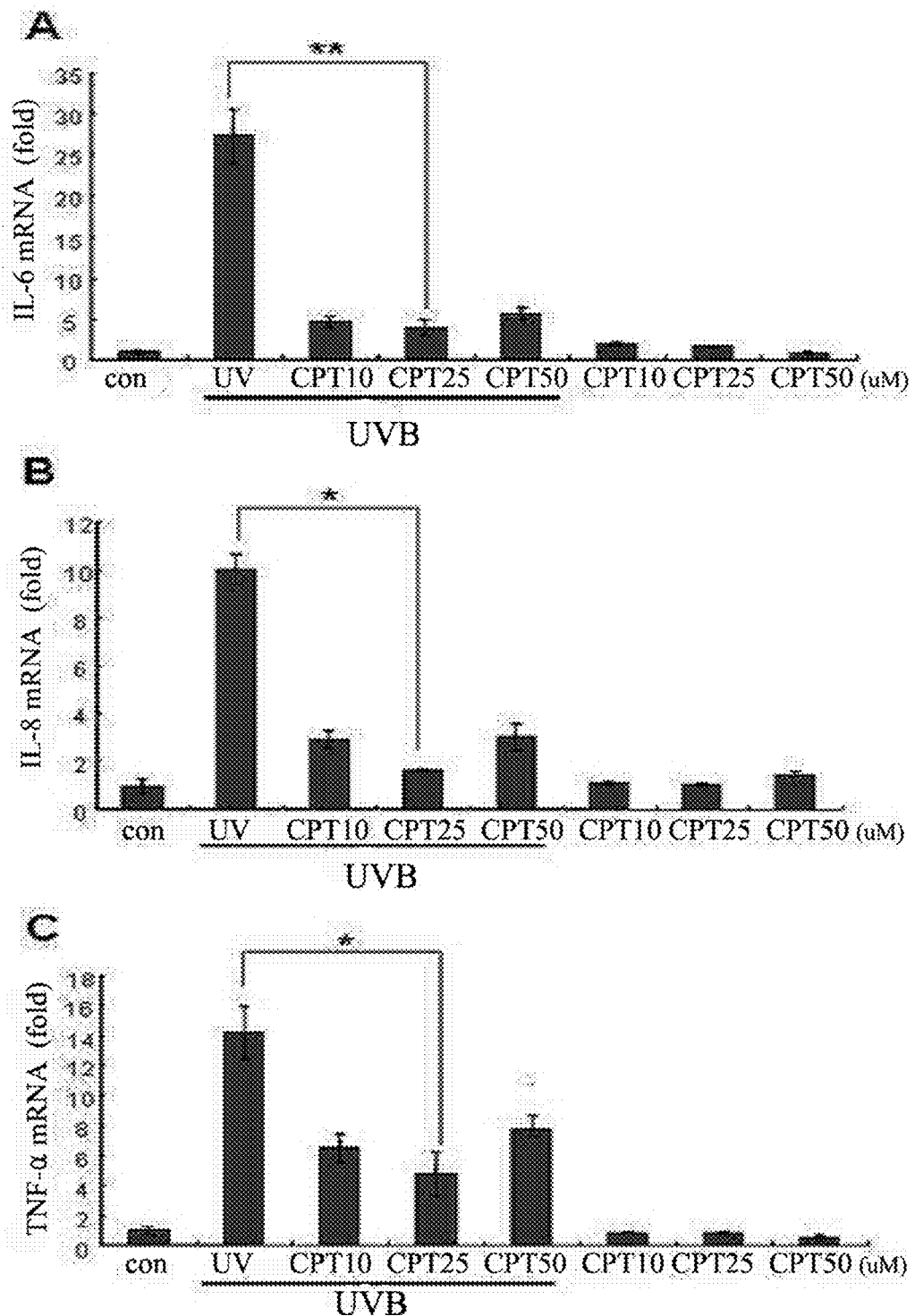
FIG. 3 shows the inhibition effect of capsiate on pro-inflammatory cytokines IL-6 (A), IL-8 (B) and TNF-α (C) (CPT10: capsiate 10 μM, CPT25: capsiate 25 μM; CPT50: capsiate 50 μM).

As a result, as shown in FIG. 3, UV irradiation to human keratinocytes (control group) resulted in increased expression of the pro-inflammatory cytokines IL-6, IL-8 and TNF-α. In contrast, the test group B which was treated with capsiate exhibited decreased expression of IL-6, IL-8 and TNF-α as compared to the control group. Thus, it was confirmed that capsiate significantly decreases the expression of IL-6, IL-8 and TNF-α increased by the UV irradiation.

Example 4

Inhibition Effect of Capsiate on UV-Induced Expression of Angiogenesis Factors 4-1. Inhibition Effect of Capsiate on VEGF Expression Inflammatory response leads to dilation of blood vessels and reddening of the skin (erythema). Continued and frequent inflammatory response may result in carcinogenesis. One of the most prominent phenomenons of the carcinogenesis is angiogenesis, which is essential in the growth of cancer cells [Fukuda R, Kelly B, Semenza G L. Vascular endothelial growth factor gene expression in colon cancer cells exposed to prostaglandin E2 is mediated by hypoxia-inducible factor 1. *Cancer Res.* 2003; 63: 23304]. During the inflammation process, infiltration of inflammatory cells occurs and various cytokines are secreted, resulting in cell migration or cell proliferation. In the process, angiogenesis factors are secreted. Accordingly, analysis on angiogenesis factors was carried out in order to investigate the effect of capsiate on these procedures.

First, the inhibition effect of capsiate on the expression of VEGF, the typical intracellular angiogenesis factor, was evaluated by immunohistochemical staining in order to investigate the inhibition effect of capsiate on angiogenesis.

HaCaT cells were placed on a 14 mm culture slide and cultured for 24 hours in DMEM containing 10% FBS. Subsequently, the cells were cultured for 24 hours in DMEM containing 1% FBS until starvation. Then, after treating with 25 μM capsiate for 30 minutes, followed by washing 3 times with PBS, UV was irradiated at an intensity of 100 $J/m^2$. Immediately after the UV irradiation, the cells were washed again with PBS and further cultured for 24 hours in DMEM containing 1% FBS, which was treated with capsiate at the same concentration as in the pre-treatment. The cells were fixed for 5 minutes using methanol and immunohistochemical staining was carried out in the same manner as in Example 2-3. For VEGF detection, rabbit anti-VEGF IgG antibody (Santa Cruz, USA) and Alexa 488-labeled anti-rabbit-IgG secondary antibody (Invitrogen, USA) were used.

Figure 4:
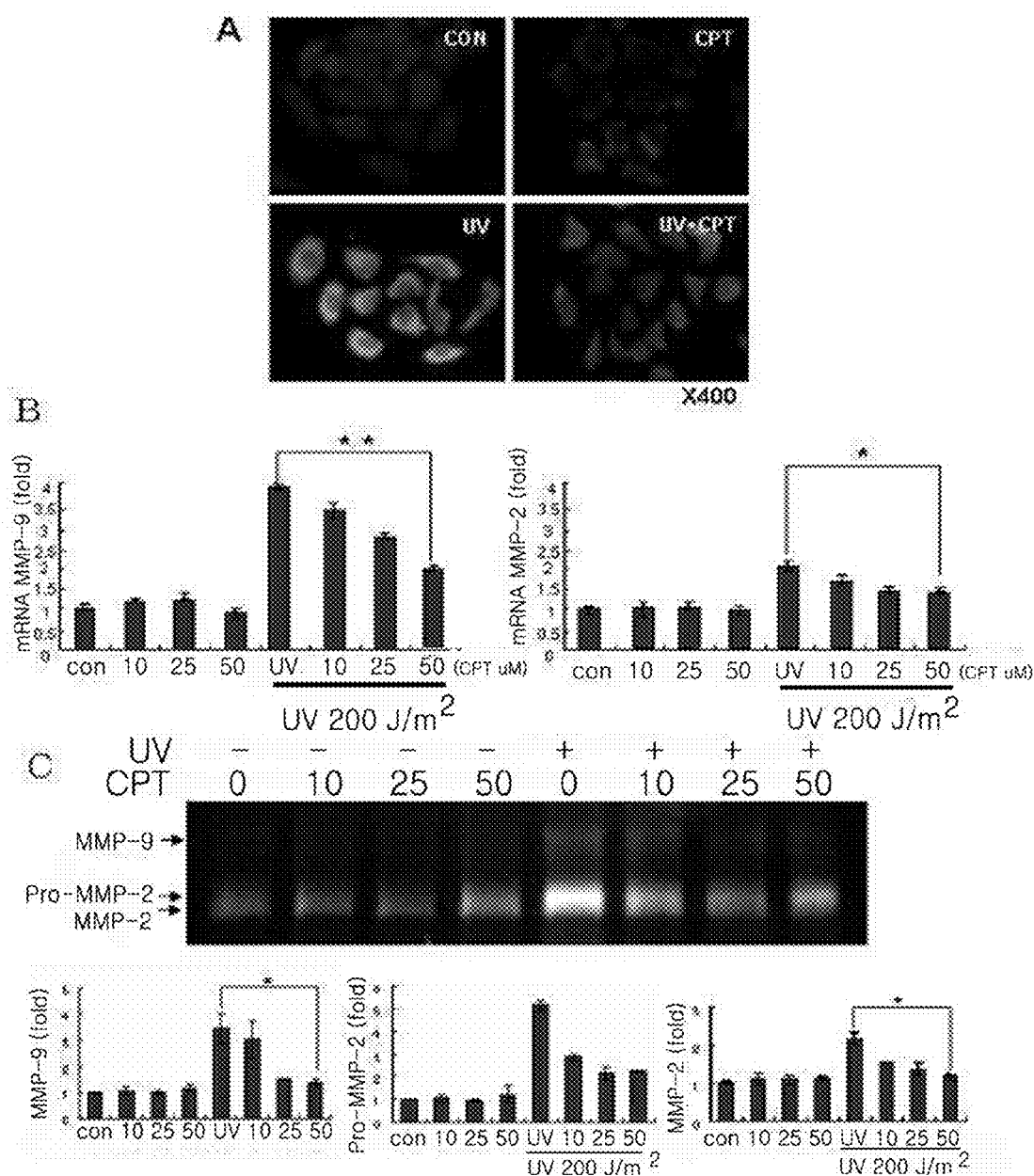
FIG. 4 shows the inhibition effect of capsiate on the expression of VEGF (A), MMP-2 (B) and MMP-9 (C) [Numbers in the abscissa in FIGS. 4B and 4C denote the addition amount of capsiate (unit: μM)].

As a result, as shown in FIG. 4A, VEGF expression increased in the control group, which was irradiated with UV only. In the test group B, which was also treated with capsiate, VEGF expression decreased. Accordingly, it was confirmed that capsiate inhibits UV-induced VEGF expression in the cytoplasm.

4-2. Inhibition Effect of Capsiate on MMP-2 and MMP-9

MMPs are induced by pro-inflammatory cytokines and are the typical angiogenesis factors expressed when angiogenesis is induced in cells due to UV, etc. [Mantena S K, Meeran S M, Elmets C A, Katuyar, S K. Orally administered green tea polyphenols prevent ultraviolet radiation induced skin cancer in mice through activation of T cells and inhibition of angiogenesis in tumors. *J. Nutr.* 2005: 135:2871-7].

The inhibition effect of capsiate on the expression of MMP-2 and MMP-9, which induce angiogenesis, was investigated through measurement of mRNA expression by RT-PCR and protein expression and activity measurement by zymography.

In order to investigate the inhibition effect of capsiate on MMP expression, $5 \times 10^5$ HaCaT cells were placed on a 60 mm Petri dish and cultured for 24 hours in DMEM containing 10% FBS. Subsequently, the cells were cultured for 24 hours in DMEM containing 1% FBS until starvation. Then, after treating with capsiate at different concentrations (10 μM, 25 μM, 50 μM) for 30 minutes, followed by washing 3 times with PBS, UV was irradiated at an intensity of 100 $J/m^2$. Immediately after the UV irradiation, the cells were washed again with PBS and further cultured for 36 hours in DMEM containing 1% FBS, which was treated with capsiate at the same concentration as in the pre-treatment. The degree of intracellular mRNA expression for MMP-2 and MMP-9 was measured by RT-PCR in the same manner as in Example 3. The degree of MMP expression was compared with that of the non-treated group.

As a result, as shown in FIG. 4B, the expression of MMP-2 and MMP-9 decreased in the test group B, which was treated with capsiate and then exposed to UV irradiation, as compared to the control group, which was irradiated with UV only. Accordingly, it seems that capsiate inhibits UV-induced mRNA expression of MMP-2 and MMP-9.

4-3. Inhibition Effect of Capsiate on MMP-2 and MMP-9

Zymography was carried out in order to investigate the decrease of expression and activity of MMP-2 and MMP-9 in protein level.

$5 \times 10^5$ HaCaT cells were placed on a 60 mm Petri dish and cultured for 24 hours in DMEM containing 10% FBS. Subsequently, the cells were cultured for 24 hours in DMEM containing 1% FBS until starvation. Then, after treating with capsiate at different concentrations (10 μM, 25 μM, 50 μM) for 30 minutes, followed by washing 3 times with PBS, UV was irradiated at an intensity of 100 J/m². Immediately after the UV irradiation, the cells were washed again with PBS and further cultured for 36 hours in DMEM containing 1% FBS, which was treated with capsiate at the same concentration as in the pre-treatment. After collecting the culture medium, the activity of MMP-2 and MMP-9 proteins secreted from the cells into the medium was measured. To this end, the mediums obtained from the same number of cells were concentrated to the same volume, and the temperature was maintained at 4° C. in order to avoid the effect on the protein activity.

Thus prepared sample was subjected to electrophoresis at 4° C. using 7.5% acrylamide gel containing gelatin but without sodium dodecyl sulfate (SDS). After washing with renaturing buffer (50 mM Tris-HCl, pH 7.4, 2.5% (v/v) Triton X-100) for 30 minutes, the sample was incubated in zymogram incubation buffer (50 mM Tris-HCl, pH 7.6, 50 mM NaCl, 10 mM $CaCl_2$, 0.05% Brij35) in a 37° C. incubator for at least 16 hours. The incubated gel was subjected to staining using 0.1% Coomassie dye to measure the activity of MMP-2 and MMP-9. As a result, as shown in FIG. 4C, the expression of pro-MMP-2, MMP-2 and MMP-9 remarkably increased in the cells exposed to UV. In contrast, the medium of the test group B, which was treated with capsiate prior to UV irradiation, exhibited inhibited expression and activity of pro-MMP-2, MMP-2 and MMP-9.

Accordingly, it was confirmed that capsiate significantly reduces UV-induced MMP expression and has excellent effect of inhibiting angiogenesis induced by inflammatory response.

Example 5

Effect of Capsiate on UV in Animal Model

In order to confirm the in vitro experiment result performed on the human keratinocyte HaCaT cells in an animal model, experiment was carried out as follows using hairless mouse (SKH-1). Test groups were as follows: non-treated group—treated with acetone only without UV irradiation; test group A—treated with 200 μL of 1 mM capsiate dissolved in acetone every 24 hours without UV irradiation; control group—treated with UV and acetone; test group B—treated with UV and 200 μL of 1 mM capsiate dissolved in acetone every 29 hours (Unspecified conditions are the same as in Examples 5-7).

Capsiate was applied on the back of the mouse. 1 hour later, UV was irradiated at an intensity of 2.5 kJ/m². 1 hour later, capsiate was applied again at the same concentration in order to prevent rash which may occur immediately after. UV irradiation. Thereafter, capsiate was applied every 24 hours and UV irradiation was carried out every other day at an intensity of 2.5 kJ/m² for 4 times. In order to investigate the change of tissue and intracellular mechanism (signaling), the mouse was euthanized 1 hour after the final UV irradiation. Skin tissue was taken from the back of the mouse and subjected to skin biopsy following observation.

Figure 5:
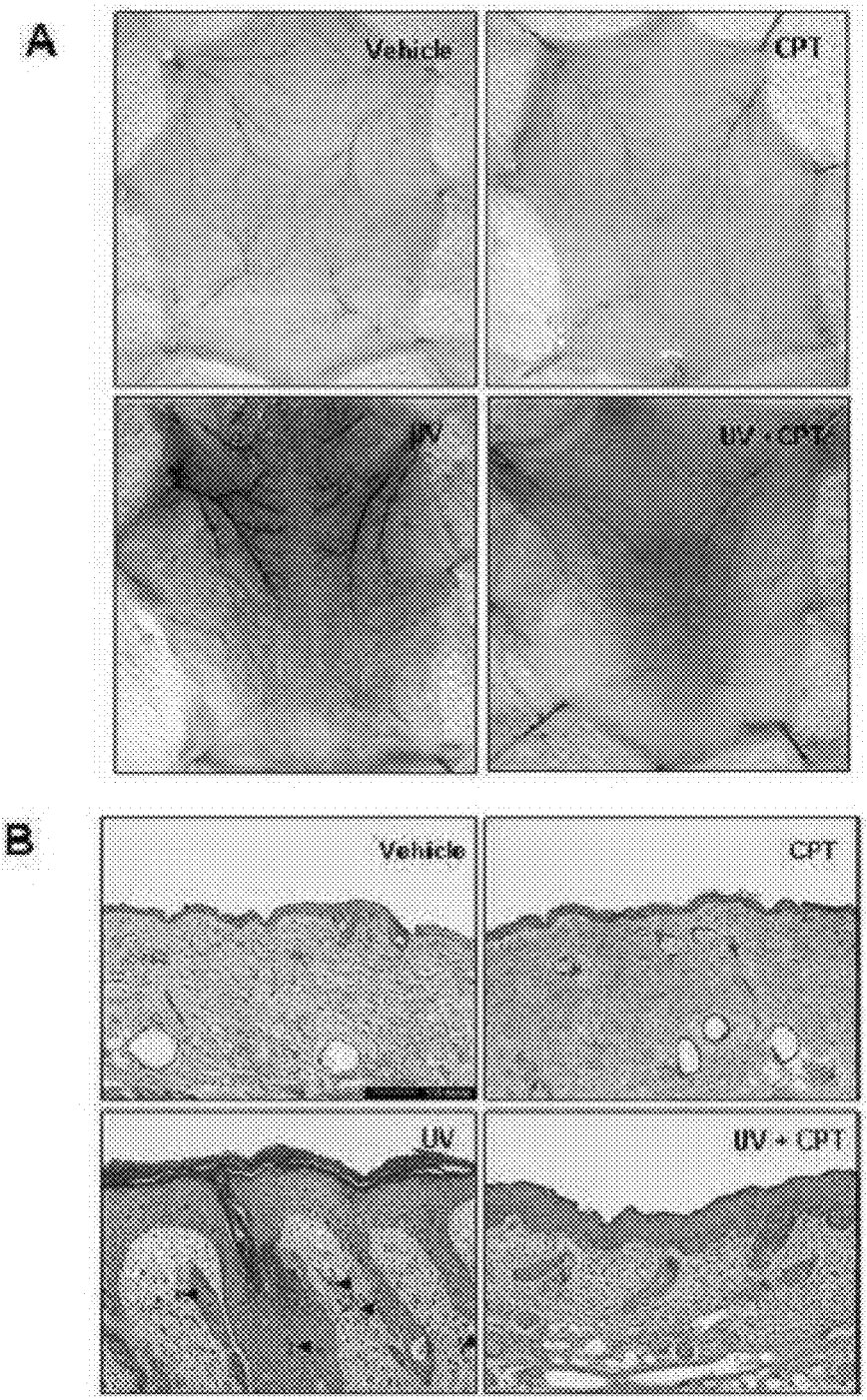
FIG. 5 shows the effect of capsiate on UV irradiation in hairless mouse (Vehicle: non-treated group).

As a result, as shown in FIG. 5A, the control group (UV) showed thick blood vessels on the back. There were a lot of blood and severe wound (inflammatory response) was observed. In contrast, when UV was irradiated after the application of capsiate (test group B, UV+CPT), the skin tissue showed less blood vessel thickness and less blood. Further, the size and depth of wound induced by UV irradiation were less severe.

Hematoxylin-eosin staining was carried out in order to investigate the overall change in the skin tissue. As shown in FIG. 5B, the non-treated group (UV) showed hyperplasia in the epidermis. In contrast, when UV was irradiated after the treatment with capsiate (test group B, UV+CPT), hyperplasia in the epidermis decreased remarkably, and blood vessels and edema were also decreased.

Accordingly, it is deemed that capsiate can effectively prevent UV-induced skin damage.

Example 6

Effect of Capsiate on UV-Induced COX-2 Expression in Animal Model 6-1. Effect of Capsiate on COX-2 Expression In the foregoing, it was confirmed that capsiate suppress inflammatory response, angiogenesis, edema, etc. caused by the UV-induced skin damage. Thus, the change of COX-2 expression and intracellular signaling was investigated by Western blotting using the mouse tissue of Example 5, in order to investigate the effect of capsiate on inflammatory response in animal model. Skin tissue was frozen in liquid nitrogen and ground finely using a mortar. After isolating proteins using RIPR buffer (2 mM EDTA, 137 mM NaCl, 20 mM Tris-HCl (pH 8.0), 1 mM sodium vanadate, 10 mM NaF, 1 mM PMSF, 1% Triton X-100, 10% glycerol, protease inhibitor cocktail), SDS-PAGE electrophoresis was carried out in acrylamide gel. After transferring to a nylon membrane, COX-2 proteins were observed using goat anti-COX-2 IgG antibody (Santa Cruz, USA) and anti-goat IgG HRP conjugated antibody (Zymed) as the secondary antibody. After detection using ECL (Amersham, Piscataway, N.J.), the proteins were visualized using RAS 3000 imaging system (Fuji Film, Japan).

Figure 6:
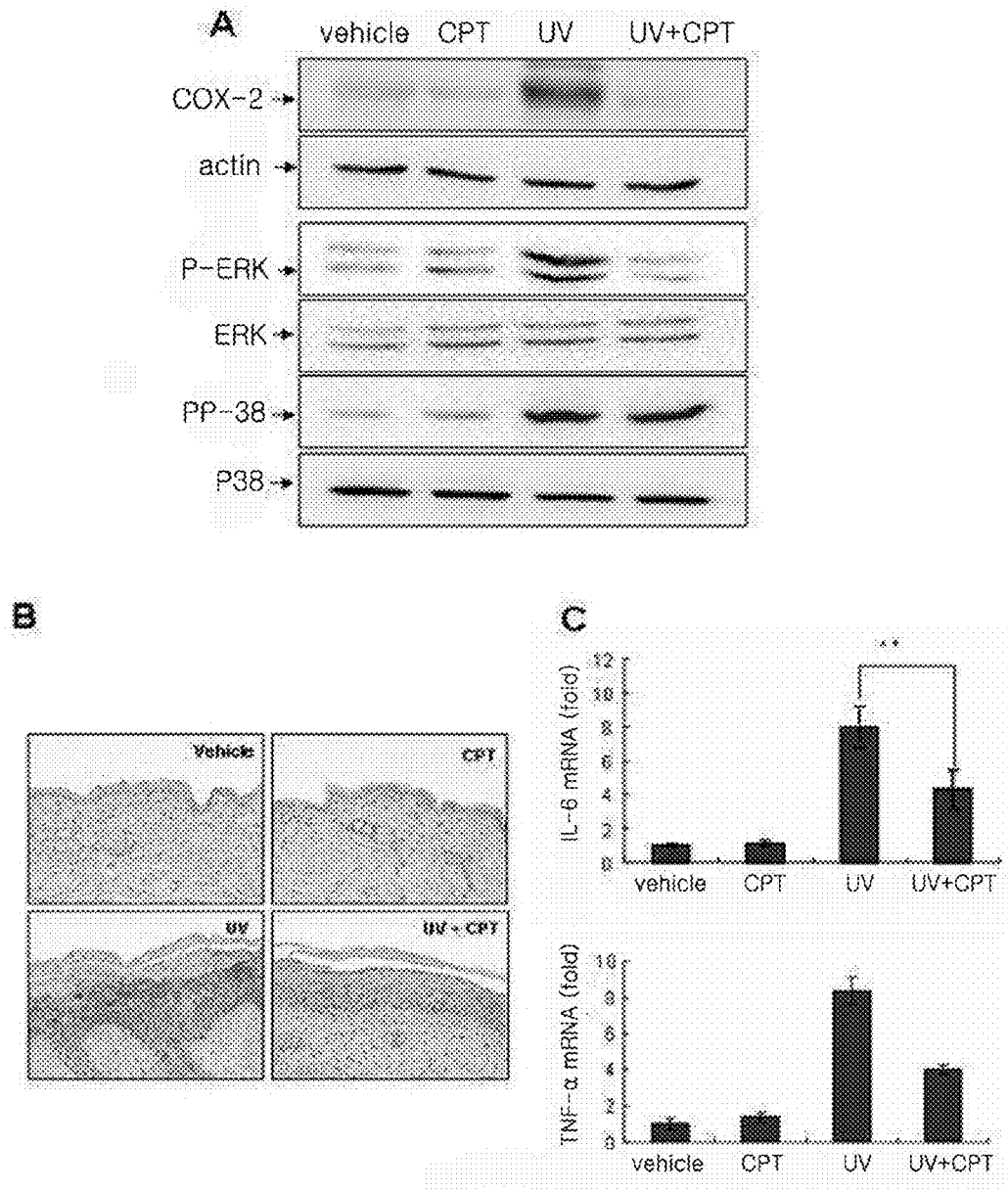
FIG. 6 shows the effect of capsiate on COX-2 (A, B), MAPK signaling (A) and expression of pro-inflammatory cytokines (C).

As a result, as shown in FIG. 6A, the expression of COX-2 induced in the mouse skin tissue through 4 times of UV irradiation was remarkably decreased by the treatment with capsiate.

6-2. Effect of Capsiate on COX-2 Expression

In order to reconfirm this effect, immunohistochemical staining was carried out as follows. Mouse skin tissue was fixed in 4% paraformaldehyde for 24 hours and then washed in flowing water for 24 hours. The tissue was dehydrated in 70, 80, 90, 95 and 100% ethanol and xylene, in sequence, and immersed in melted paraffin so that the tissue was soaked with paraffin. Thus prepared paraffin-embedded tissue was sliced with a thickness of 5 μm and fixed on a slide. The slide was treated with xylene, 100, 95, 90, 80 and 70% ethanol and sterilized distilled water to remove paraffin. Then, after carrying out epitope retrieval using 10 mM sodium citrate buffer (0.05% Tween 20, pH 6.0), peroxidase was removed from the cells using hydrogen peroxide ($H_2O_2$), followed by blocking with 10% normal goat serum for 1 hour. The blocked tissue was washed 3 times with PBS and treated with COX-2 antibody (1:100, Santa Cruz, USA) diluted in 10% normal goat serum. After incubation at 4° C. for at least 16 hours, the tissue was washed 3 times with PBS. After treatment with biotinylated secondary antibody (DAKO code K0675; Carpinteria, DAKO) for 30 minutes, the tissue was washed 3 times. After treating with streptavidin-peroxidase (DAKO code K0675) for 30 minutes, followed by washing 3 times with PBS, the tissue was stained with 3,3'-diaminobenzidine (DAB) (DAKO). The stained tissue was dehydrated, fixed on a slide, and observed under an optical microscope.

As a result, as shown in FIG. 6B, UV induced significant increase of COX-2, which was effectively inhibited by capsiate.

6-3. Confirmation of Mechanism by which COX-2 Expression is Inhibited

In order to investigate the intracellular mechanism (signaling) related with the inhibition of COX-2 expression by capsiate, Western blotting was carried out for MAPK signaling-related proteins (ERK, p-ERK, p38, p-p38 and JNK, p-JNK) as in Example 2-2, using proteins isolated from the mouse skin tissue.

As a result, as shown in FIG. 6A, there was no significant difference when P38 and JNK were exposed to UV after treatment with acetone only (UV) and in the test group where they were exposed to UV after treatment with capsiate (UV+CPT). However, for ERK, the test group which was exposed to UV after treatment with capsiate exhibited suppressed phosphorylation.

Accordingly, it was confirmed as in Example 2-2 that capsiate regulates COX-2 expression and intracellular change related thereto through inhibiting ERK phosphorylation.

6-4. Inhibition Effect of Capsiate on Pro-Inflammatory Cytokines

In order to investigate the effect of capsiate on the production of IL-6 and TNF-α induced in skin tissue during inflammatory response, the inhibition ability of capsiate against the expression of the pro-inflammatory cytokines was evaluated in animal model as follows. Test groups were as follows: non-treated group—treated with acetone only without UV irradiation; test group A—treated with 200 μL of 1 mM capsiate dissolved in acetone without UV irradiation; UV group—treated with acetone and UV; test group B—treated with 200 μL of 1 mM capsiate dissolved in acetone followed by UV irradiation 1 hour later.

To this end, acetone and capsiate were treated prior to UV irradiation. After treating with UV once at an intensity of 5 kJ/m$^2$, hairless mouse was euthanized 6 hours later. mRNA was extracted from the mouse tissue obtained by skin biopsy and RT-PCR was carried out as follows. For RNA extraction from the tissue, each mouse tissue obtained by skin biopsy was quickly frozen in liquid nitrogen and ground finely using a mortar. RNA was extracted from the mouse tissue using Trizol (Invitrogen, USA), and PCR (PTC-225 Peltier thermal cycler, MJ Research, USA) was carried out using it as template and using a commercial kit (reverse transcription system, Qiagen, USA). As a result, cDNA was prepared from each group.

RT-PCR (Rotor Gene 6 series, Corbett Research, Australia) was carried out using each prepared cDNA was used as template and using IL-6 and TNF-α primers (Qiagen, USA). mRNA expression for intracellular pro-inflammatory cytokines was normalized using glyceraldehyde-3-phosphate dehydrogenase (GAPDH). The level of expression was compared with that of the non-treated group, which was treated with acetone only.

As a result, as shown in FIG. 6C, capsiate resulted in the decrease of UV-induced expression of IL-6 and TNF-α. Thus, it is deemed that capsiate can effectively regulate inflammatory response by inhibiting the production of pro-inflammatory cytokines in UV-induced inflammatory response.

Example 7

Inhibition Effect of Capsiate on Angiogenesis Factors in Animal Model Using Hairless Mouse In order to investigate the effect of capsiate on various intracellular angiogenesis-related expression factors, the inhibition effect of capsiate on angiogenesis factors induced by UV was evaluated using the mouse tissue of Example 5.

7-1. Inhibition Effect of Capsiate on Ki67

Ki67 is a protein involved in the proliferation of cells and its expression is increased in the epidermal basal layer during inflammatory response and carcinogenesis [Boland G P, Butt I S, Prasad R, et al. COX-2 expression is associated with an aggressive phenotype in ductal carcinoma in situ. *Br. J. Cancer* 2004; 90:423429]. Its expression is also increased by UV irradiation. Immunohistochemical staining was carried out as follows in order to confirm the effect of capsiate on Ki67.

Mouse skin tissue obtained by skin biopsy was immersed in OCT compound (Sakura Finetechnical Co. Ltd, Japan) and slowly frozen in liquid nitrogen. Thus prepared tissue was sliced with a thickness of 7 μm and fixed on a slide using acetone. The tissue was washed with distilled water and PBS and, after blocking for 1 hour using 10% normal goat serum, incubated at 4° C. for at least 16 hours using ki67 antibody (1:100, Neomarker, USA). After washing 3 times with PBS, the tissue was treated with Alexa 488-conjugated secondary antibody (Invitrogen, USA) for 30 minutes and then washed 3 times. The tissue was mounted and observed under a fluorescence microscope (Carl Zeiss, USA).

Figure 7:
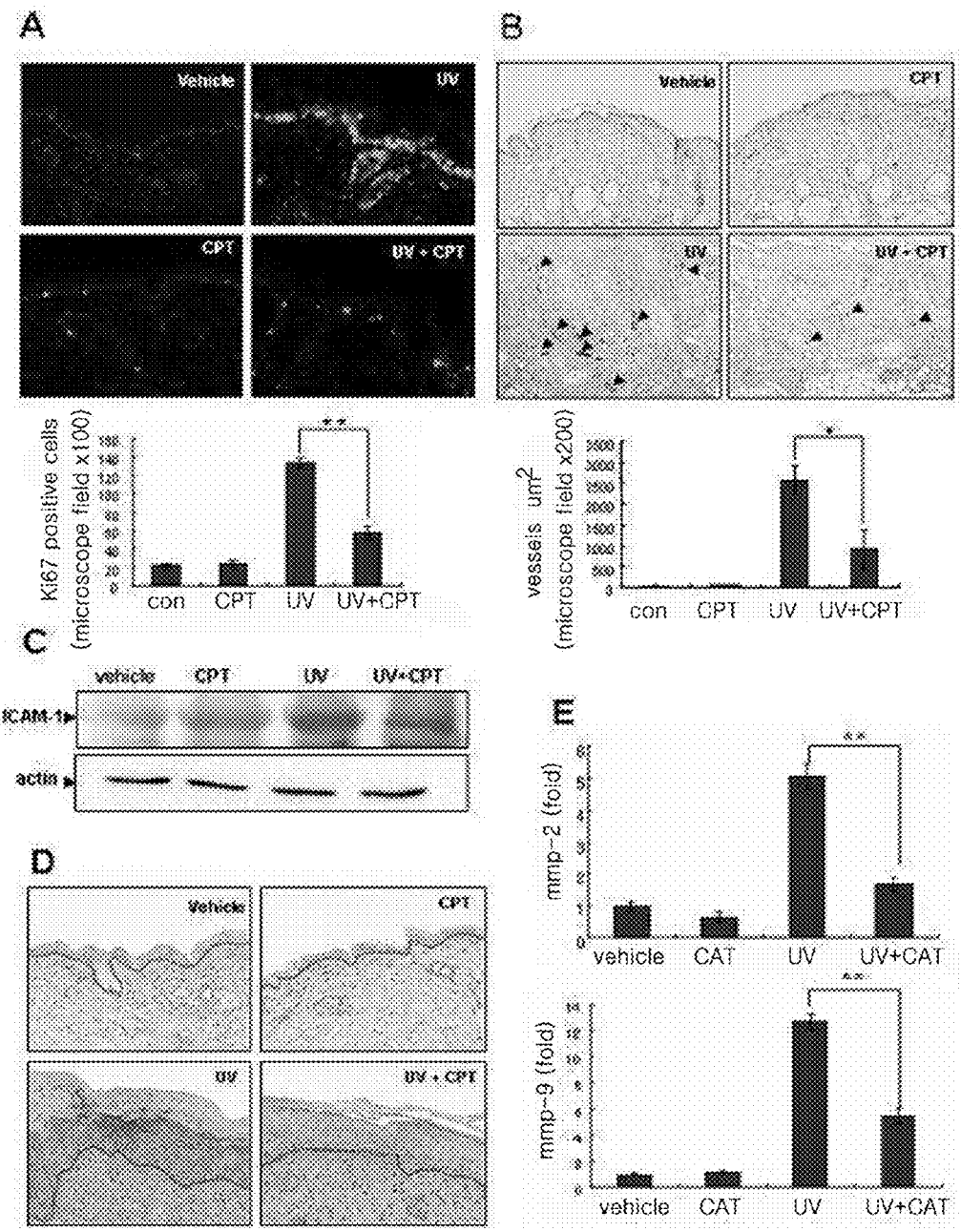
FIG. 7 shows the effect of capsiate on the expression of angiogenesis factors Ki67 (A), PECAM-1 (B), ICAM-1 (C), VEGF (D) and MMP-2 and MMP-9 (E).

As a result, as shown in FIG. 7A, the expression of Ki67, which was remarkably increased by UV, was significantly inhibited by the treatment with capsiate.

7-2. Inhibition Effect of Capsiate on PECAM-1

PECAM-1 (CD31), an angiogenesis recognizing molecule along with Ki67, is an endothelial marker the expression of which increases mainly in the blood vessel walls during angiogenesis. Accordingly, the effect of capsiate in angiogenesis can be observed by investigating the level of PECAM-1 expression.

To investigate this effect, the paraffin-embedded tissue prepared as in Example 6 was processed in the same manner as Example 6, treated with PECAM-1 antibody (1:100, BD Pharmingen, USA) on a slide, treated with biotinylated secondary antibody (DAKO code K0675; DAKO Corp., USA) for 30 minutes, and washed 3 times. After treatment with streptavidin-peroxidase (DAKO code K0675, DAKO Corp., USA) for 30 minutes, followed by washing 3 times with PBS, the tissue was stained using DAB (DAKO Corp., USA) for confirmation of the level of PECAM-1 expression.

As a result, as shown in FIG. 7B, UV irradiation resulted in increased PECAM-1 expression inside the blood vessel walls mainly in the dermis of the skin tissue. However, when capsiate was treated prior to the UV irradiation, the level of PECAM-1 expression was significantly lower.

7-3. Inhibition Effect of Capsiate on ICAM-1

Western blotting was carried out in the same manner as Example 6 using the proteins isolated from the mouse skin tissue of each test group in Example 6, in order to investigate the level of expression of ICAM-1 (CD54), which is involved in cell infiltration, cell migration, angiogenesis, etc. in inflammatory response. In order to investigate the level of ICAM-1 expression, mouse anti-ICAM-1 antibody (Santa Cruz, USA) and HRP-conjugated secondary antibody (1:10,000, Zymed) were used.

As a result, as shown in FIG. 7C, the level of ICAM-1 expression, which increased by UV irradiation, decreased in the mouse skin tissue of the test group B, which was treated with capsiate prior to the UV irradiation.

7-4. Inhibition Effect of Capsiate on VEGF

Western blotting was carried out in the same manner as Example 6 using the proteins isolated from the mouse skin tissue of each test group in Example 6, in order to investigate of capsiate on VEGF, which plays an important role in angiogenesis. In order to investigate the level of VEGF expression, VEGF antibody (Santa Cruz, USA) and HRP-conjugated secondary antibody (1:10,000, Zymed) were used.

As a result, as shown in FIG. 7D, UV irradiation induced the secretion of VEGF over the epidermal and dermal layers. When was treated prior to the UV irradiation, the level of VEGF expression in the mouse skin tissue decreased.

7-5. Inhibition Effect of Capsiate on MMP-2 and MMP-9 mRNA was extracted from the mouse tissue of each test group of Example 5 and the level of expression thereof was evaluated in order to investigate the effect of capsiate on the expression of MMP-2 and MMP-9 induced by angiogenesis and immune response.

For RNA extraction from the tissue, each mouse tissue was subjected to skin biopsy, quickly frozen in liquid nitrogen and finely ground using a mortar. RNA was extracted from the mouse tissue using Trizol (Invitrogen, USA). PCR (PTC-225 Peltier thermal cycler, MJ Research, USA) was carried out using the RNA as template and using a commercial kit (reverse transcription system, Qiagen, USA). As a result, cDNA for each test group was prepared.

RT-PCR (Rotor Gene 6 series, Corbett Research, Australia) was carried out using thus prepared cDNA as template and using MMP-2 and MMP-9 primers (Qiagen, USA). The level of mRNA expression for MMP was normalized using GAPDH. The level of expression was compared with that of the non-treated group, which was treated with acetone only.

As a result, as shown in FIG. 7E, the expression of MMP-2 and MMP-9 increased remarkably by UV irradiation. When capsiate was treated, the expression of MMP-2 and MMP-9 decreased.

Thus, it is deemed that capsiate can effectively suppress angiogenesis mediated by inflammatory response and can act as inflammation and cancer inhibitor.

Example 8

Inhibition Effect of Capsiate on UV-Induced Erythema 8-1. Effect of Capsiate on Erythema When the skin is exposed to UV, erythema, or rudeness of the skin, occurs accompanied by edema, prior to a variety of cellular changes including inflammation, apoptosis, carcinogenesis, or the like [Tadashi Terui, Hachiro Tagami, Mediators of inflammation involved in UVB erythema, *Journal of Dermatological Science* 23 Suppl. 1 (2000) S1S5]. In order to investigate the effect of capsiate on erythema accompanied by UV-induced inflammatory response, experiment was carried out as follows using hairless mouse. Test groups were as follows: non-treated group—treated with acetone only without UV irradiation; test group A—treated with 200 µL of 1 mM capsiate dissolved in acetone without UV irradiation; UV group—treated with acetone and UV; test group B—treated with UV and 200 µL of 1 mM capsiate dissolved in acetone every 24 hours.

Acetone or capsiate diluted in acetone was applied on the back of the mouse of each test group. 1 hour later, a mask was attached on the back of the mouse such that UV could be irradiated only on an area of 1.2 cm×1.2 cm. UV was irradiated at an intensity of 400, 600 and 800 J/m$^2$. The degree of erythema was measured 48 hours later.

Figure 8:
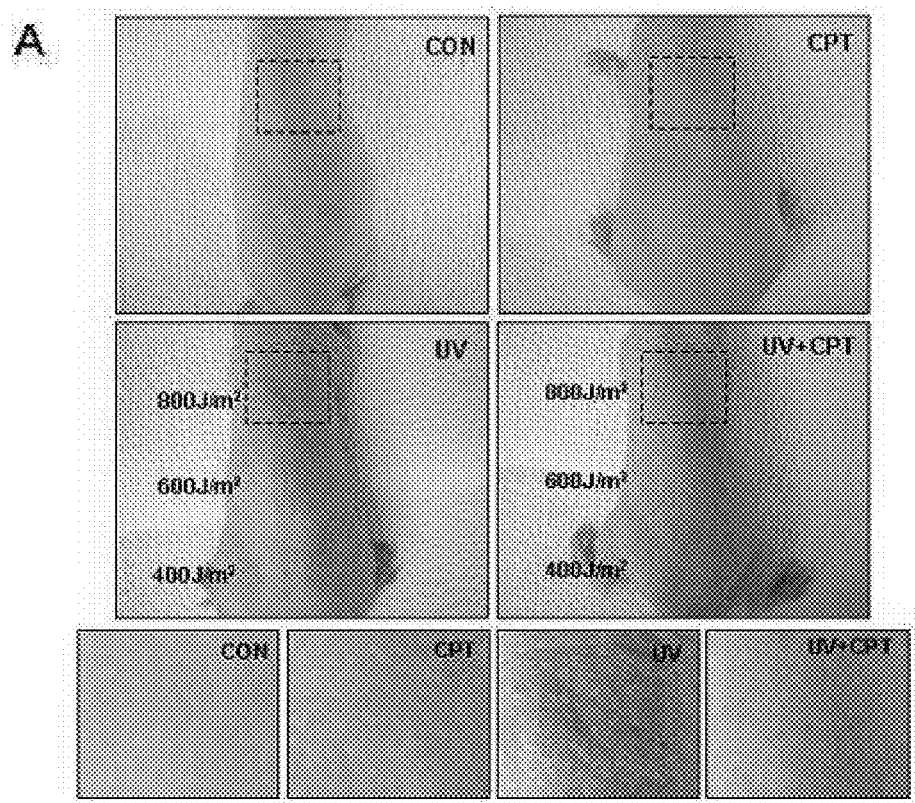
FIG. 8 shows the effect of capsiate on UV-induced erythema (A) and skin tissues (B).
Figure 8:
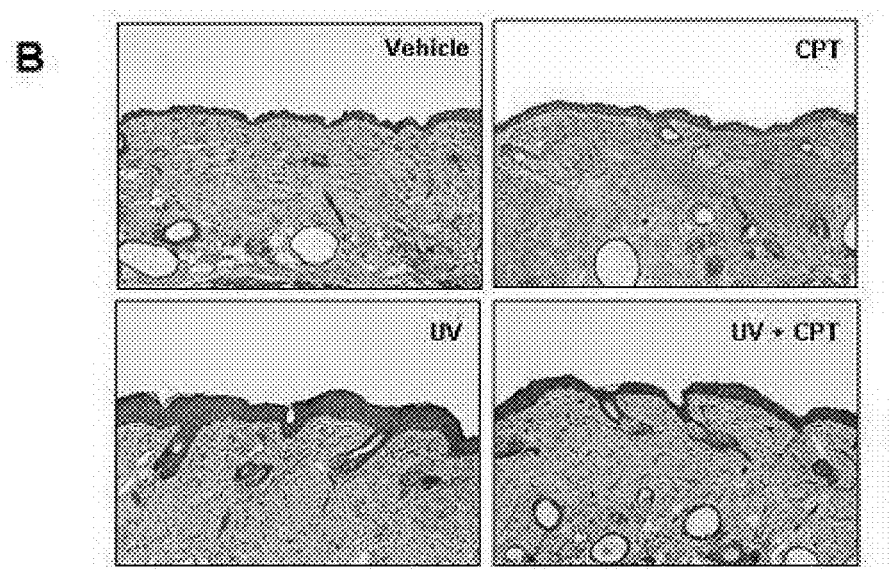

As a result, as shown in FIG. 8A, the degree of erythema was severer in proportion to the intensity of UV irradiation. When UV was irradiated after treatment with capsiate, the degree of erythema was weaker.

8-2. Effect of Capsiate on Change of Skin Tissue

After 4 times of UV irradiation every other day at an intensity of 2.5 kJ/m$^2$, hematoxylin-eosin staining was carried out in order to observe the change of mouse skin tissue.

As a result, as shown in FIG. 8B, the epidermis became thicker upon UV irradiation. However, when capsiate was treated prior to the UV irradiation, the epidermis was less thick.

Accordingly, it was confirmed that capsiate can effectively inhibit the skin erythema induced by UV irradiation.

Example 9

Inhibition of VEGF-Induced Proliferation of Endothelial Cells 9-1. Confirmation of Effect on Proliferation of Endothelial Cells MTT assay was carried out investigate the effect of capsiate or dihydrocapsiate on the proliferation of endothelial cells (EC) induced by VEGF.

Human umbilical vein endothelial cells (HUVEC) were placed on a gelatin-coated 24-well plate at a concentration of $2 \times 10^4$ cells/well. After culturing for 24 hours, followed by washing twice with M199 medium (Invitrogen, USA), the cells were cultured for 6 hours in M199 medium containing 1% FBS. After addition of capsiate or dihydrocapsiate at different concentrations (1 µM, 5 µM, 10 µM, 25 µM), followed by pre-culturing for 30 minutes, 10 ng/mL VEGF (Upstate, USA) was added and the cells were cultured for 48 hours. Then, 3-(4,5-dimethylthiazol-2-yl)-2,5-diphenyltetrazolium bromide salt (MTT) solution (0.5 mg/mL) was added and the cells were cultured at 37° C. for 3 hours. Remaining MTT was cautiously removed and the formed crystal was dissolved in DMSO for 30 minutes and subjected to absorbance measurement at 560 nm after mixing well for 5 minutes.

Figure 9:
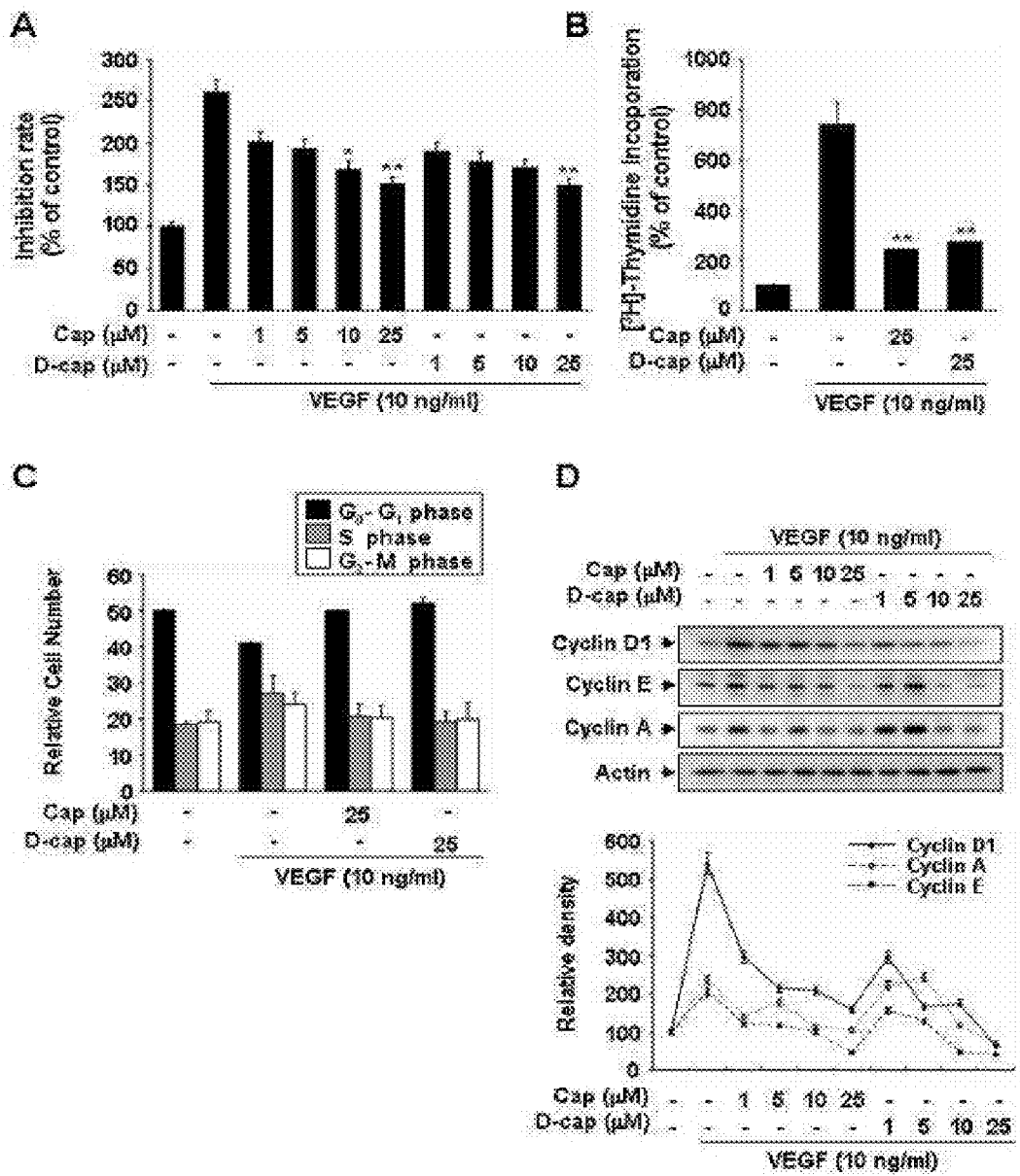
FIG. 9 shows the effect of capsiate and dihydrocapsiate on the proliferation of endothelial cells evaluated through MTT assay (A) and 3H-thymidine incorporation assay (B) as well as the change of cell cycle of endothelial cells (C) and the change of cyclin proteins (D) (D-cap: dihydrocapsiate).

As a result, as shown in FIG. 9A, the proliferation of HUVEC induced by VEGF was inhibited by capsiate or dihydrocapsiate in a concentration-dependent manner. Considering that the HUVEC cells grew normally when the concentration of capsiate or dihydrocapsiate was increased up to 50 µM without VEGF irritation, the inhibition effect of capsiate or dihydrocapsiate is not deemed due to cell toxicity (not shown in figure).

9-2. Confirmation of Effect on Proliferation Endothelial Cells

The inhibition effect of capsiate or dihydrocapsiate on the proliferation of EC induced by VEGF was investigated by $^3$H-thymidine incorporation assay according to a method published in the literature [Lee O H et al., 1999, *Biochem. Biophys. Res. Commun.*, 264: 743-750].

In brief, HUVEC were placed on a gelatin-coated 24-well plate at a concentration of $2 \times 10^4$ cells/well. After culturing for 24 hours, followed by washing twice with M199 medium (Invitrogen, USA), the cells were cultured for 6 hours in M199 medium containing 1% FBS. After addition of 25 μM capsiate or dihydrocapsiate, followed by pre-culturing for 30 minutes, 10 ng/mL VEGF was added and the cells were cultured for 30 hours. Then, 0.5 μCi/mL $^3$H-thymidine was added and the cells were cultured for 6 hours.

DNA was precipitated from the cultured cells in 10% trichloroacetic acid at 4° C. for 30 minutes and washed twice with water. The DNA was dissolved in 0.2 N NaOH/0.1% SDS and measured using a liquid scintillation counter.

As a result, as shown in FIG. 9B, VEGF increased DNA synthesis in HUVEC, whereas capsiate or dihydrocapsiate inhibited the DNA synthesis.

Example 10

Confirmation of Mechanism by which Proliferation of Endothelial Cells is Inhibited 10-1. Analysis of Cell Cycle Change In order to identify the mechanism of the inhibition of proliferation of endothelial cells confirmed in Example 9, fluorescence-activated cell sorting (FACS) analysis was carried out on the cells at different phases of cell cycle.

$3 \times 10^5$ HUVEC were placed on a 60 mm plate and cultured for 24 hours. After washing twice with M199 medium (Invitrogen, USA), the cells were cultured in M199 medium containing 1% FBS for 6 hours. After adding capsiate or dihydrocapsiate at different concentrations (1 μM, 5 μM, 10 μM, 25 μM), followed by pre-culturing for 30 minutes, 10 ng/mL VEGF was added and the cells were cultured for 20 hours. Then, the cells were fixed with ethanol cooled in ice. The fixed cells were dehydrated in PBS containing 2% FBS and 0.1% Tween 20 at 4° C. for 30 minutes. After centrifuge, the cells were lysed in the same buffer solution. After treating with RNase (37° C., 1 hr), followed by staining with propidium iodide, analysis was carried out using a FACS analyzer (FACScan DB PharMingen flow cytometer).

As a result, as shown in FIG. 9C, treatment with VEGF resulted in the decrease of the number of HUVEC in $G_1$ arrest phase as compared to the control group. In contrast, treatment with capsiate or dihydrocapsiate resulted in the increase of the number of endothelial cells in $G_1$ arrest phase. Accordingly, it was confirmed that capsiate or dihydrocapiate affects the transition from $G_1$ to S phase.

10-2. Confirmation of Effect on Cyclin D1

Since the transition from $G_1$ to S phase is partially regulated by cyclin D1, the effect of capsiate or dihydrocapsiate on cyclin D1 was investigated.

$3 \times 10^5$ HUVEC were placed on a 60 mm plate and cultured for 24 hours. After washing twice with M199 medium (Invitrogen, USA), the cells were cultured in M199 medium containing 1% FBS for 6 hours. After adding capsiate or dihydrocapsiate at different concentrations (1 μM, 5 μM, 10 μM, 25 μM), followed by pre-culturing for 30 minutes, 10 ng/mL VEGF was added and the cells were cultured for 12 hours. The cells were collected and proteins obtained therefrom were quantitated and the expression level the proteins was identified by Western blotting using antibodies of cyclin D1, cyclin E and cyclin A.

As a result, as shown in FIG. 9D, treatment with VEGF resulted in the increase of cyclin D1 expression in protein level, whereas capsiate or dihydrocapsiate resulted in a concentration-dependent decrease thereof. Further, treatment with VEGF resulted in the increase of cyclin E and cyclin A expression in protein level, whereas capsiate or dihydrocapsiate resulted in a concentration-dependent decrease thereof.

Accordingly, it was confirmed that capsiate or dihydrocapsiate inhibits the progress of cell cycle induced by VEGF by interrupting the transition from $G_1$ to S phase through lowering cyclin D1 expression.

Example 11

Inhibition of Migration and Tube Formation Induced by VEGF 11-1. Confirmation of Effect on Chemotactic Mobility Transwell assay (Corning Costar, USA) was carried out in order to investigate the effect of capsiate or dihydrocapsiate on chemotactic mobility of HUVEC [Lee O H et al., 1999, Biochem. Biophys. Res. Commun. 264; 743-750].

Figure 10:
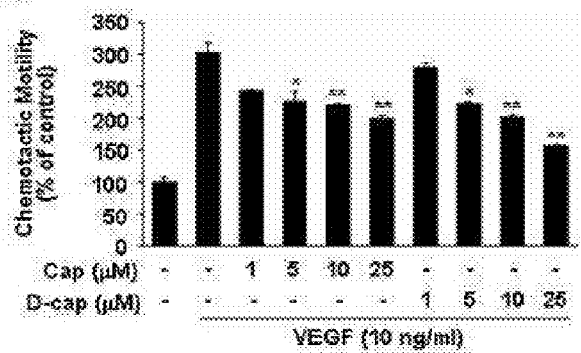
FIG. 10 shows the effect of capsiate and dihydrocapsiate on chemotactic mobility (A) and tube formation (B, C).
Figure 10:
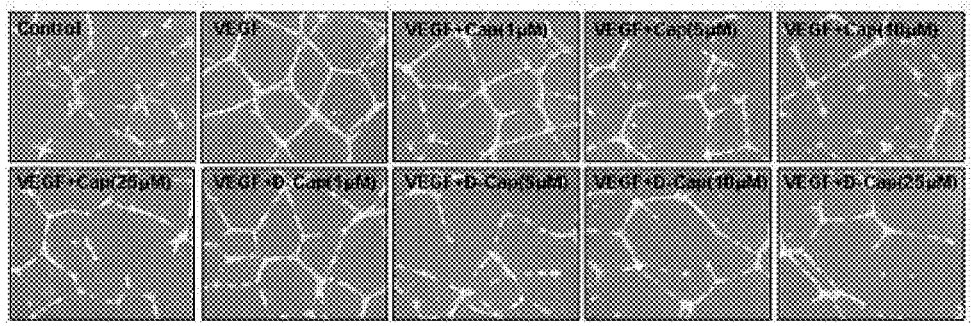
Figure 10:
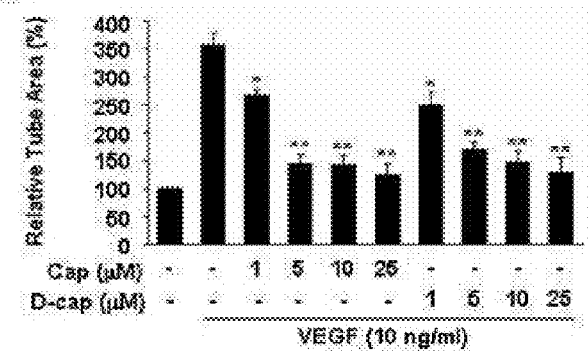

In brief, the bottom side of a filter was coated with 10 μg of gelatin and M199 medium containing VEGF and 1% FBS was added to the lower well. HUVEC were prepared by treating with trypsin and diluting in M199 medium containing 1% FBS to a concentration of $1 \times 10^6$ cells/mL. Capsiate or dihydrocapsiate at different concentrations (1 μM, 5 μM, 10 μM, 25 μM) were pre-treated at room temperature for 30 minutes. The cells in 100 mL of medium were added to the upper well and cultured at 37° C. for 4 hours. After fixation, followed by staining with hematoxylin and eosin, the cells remaining on the top surface of the filter without moving were removed. The cells that migrated to the bottom side of the filter were observed and counted using an optical microscope (×200). As a result, as shown in FIG. 10A, treatment of HUVEC with VEGF resulted in increased chemotactic mobility. However, it decreased in a concentration-dependent manner when capsiate or dihydrocapsiate was treated.

11-2. Confirmation of Effect on Tube Formation

The effect of capsiate or dihydrocapsiate on tube formation was investigated according to a method published in the literature [Lee O H et al., 1999, Biochem. Biophys. Res. Commun. 264; 743-750].

In brief, 250 μL of growth factor-reduced Matrigel (10 mg protein/mL) was added to a 16 mm tissue culture well and subjected to polymerization at 37° C. for 30 minutes. HUVEC cultured for in M199 medium containing 1% FBS for 6 hours were treated with trypsin, collected, and resuspended in M199 medium containing 1% FBS. Capsiate or dihydrocapsiate at different concentrations (1 μM, 5 μM, 10 μM, 25 μM) were pre-treated at room temperature for 30 minutes. The cells were added to the Matrigel at a concentration of $1.8 \times 10^5$ cells/well and VEGF (10 ng/mL) was added. After culturing for 20 hours, photograph was taken (×200) and the area covered by the tube network was measured according to an optical imaging technique [scanned with Adobe Photoshop and measured with Image-Pro Plus (Media Cybermetics).

As a result, as shown in FIGS. 10B and 10C, treatment of HUVEC with VEGF resulted in the formation of tube-like structures. However, it was reduced when the cells were treated with capsiate or dihydrocapsiate.

Example 12

Inhibition of VE-Cadherin Phosphorylation and Permeability of Endothelial Cells Induced by VEGF 12-1. Confirmation of Inhibition Effect on Permeability of Endothelial Cells

[$^{14}$C] sucrose permeability assay was carried out in order to identify the effect of capsiate or dihydrocapsiate on VEGF-induced endothelial permeability. In brief, HUVEC were placed on a transwell filter (Corning Costar). At confluence, the cells were cultured in M199 medium containing 1% FBS for 3 hours. After treating with capsiate or dihydrocapsiate at different concentrations (5 µM, 10 µM, 25 µM) for 30 minutes, the cells were treated with VEGF (50 ng/mL) for 1 hour. [$^{14}$C] sucrose (0.8 µCi/mL, 50 µL) was added to the upper compartment. 30 minutes later, the irradiation level was measured at the lower compartment using a scintillation counter (Wallac, PerkinElmer).

Figure 11:
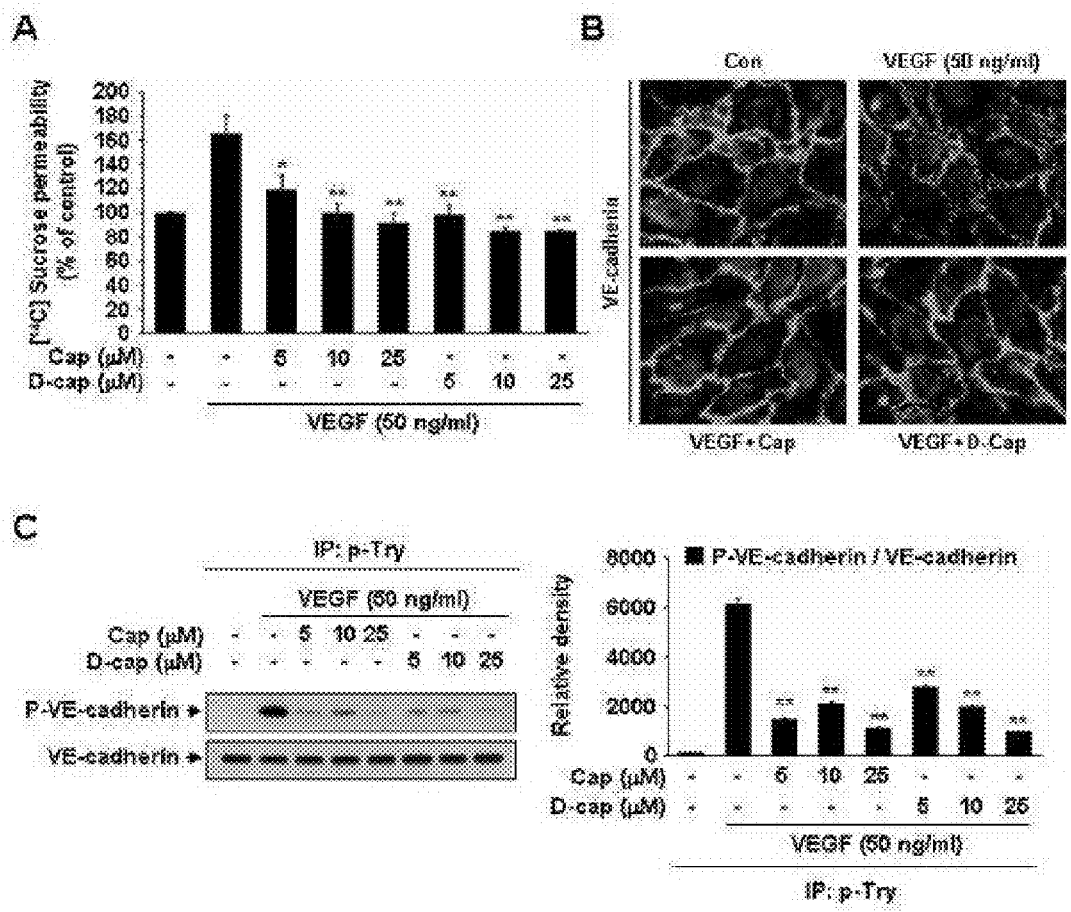
FIG. 11 shows the effect of capsiate and dihydrocapsiate on permeability of endothelial cells (A), expression (intracellular adhesion) (B) and phosphorylation (C) of VE-cadherin.

As a result, as shown in FIG. 11A, treatment with VEGF resulted in increased permeability of endothelial cells. However, it decreased in a concentration-dependent manner when the cells were treated with capsiate or dihydrocapsiate.

12-2. Confirmation of Effect on VE-Cadherin Expression

In order to identify if the change of permeability of endothelial cells is related with VE-cadherin, the level of VE-cadherin expression in the intercellular junction was investigated.

HUVEC were placed on a gelatin-coated cover slip at a concentration of 12×10$^5$ cells/well and cultured for 24 hours. After washing twice with M199 medium, the cells were cultured in M199 medium containing 1% for 6 hours. After treating with capsiate or dihydrocapsiate at different concentrations (5 µM, 10 µM, 25 µM) for 30 minutes, the cells were treated with VEGF (50 ng/mL) for hour. The cells were fixed and made permeable by treating with 2% formaldehyde for 10 minutes, and washed 3 times with PBS. Subsequently, the cells were treated with 0.1% Triton X-100 and 2% bovine serum albumin (BSA)/PBS blocking solution for 30 minutes. After labeling with VE-cadherin at room temperature for 2 hours, followed by washing with PBS, the cells were labeled again with FITC-conjugated secondary antibody at room temperature for 1 hour and 30 minutes. The cover slip was mounted on SloFade (Molecular Probes) and observed under a fluorescence microscope (Carl Zeiss).

As a result, as shown in FIG. 11B, treatment with VEGF resulted in significant decrease of cell adhesion ability of VE-cadherin in the intercellular junction, which may lead to increased permeability and migration of endothelial cells. However, when the cells were pre-treated with capsiate or dihydrocapsiate, the cell adhesion ability was recovered.

12-3. Confirmation of Effect on VE-Cadherin Phosphorylation

Because VEGF is known to induce tyrosine phosphorylation of VE-cadherin and thereby regulate permeability between endothelial cells by making the intercellular contact loose [Esser S. et al., 1998, *J. Cell Sci.*, 111: 1853-1865], the inhibition effect on tyrosine phosphorylation of VE-cadherin was investigated.

3.5×10$^5$ HUVEC were placed on a 60 mm plate and cultured for 24 hours. After washing twice with M199 medium (Invitrogen, USA), the cells were cultured in M199 medium containing 1% FBS for 6 hours. After, treating with capsiate or dihydrocapsiate at different concentrations (5 µM, 10 µM, 25 µM) for 30 minutes, followed by pre-culturing for 30 minutes, the cells were cultured for 6 hours after adding 50 ng/mL VEGF. Proteins were collected from the cells and, after quantitation, subjected to Western blotting using VE-cadherin antibody in order to identify the level of protein expression.

As a result, as shown in FIGS. 11C and 11D, treatment with VEGF induced phosphorylation of VE-cadherin. However, when the cells were treated with capsiate or dihydrocapsiate, the phosphorylation decreased in a concentration-dependent manner.

Accordingly, it was confirmed that capsiate or dihydrocapsiate inhibits tyrosine phosphorylation of VE-cadherin and, thereby, inhibits VEGF-induced permeability.

Example 13

Inhibition of VEGF-Induced Angiogenesis 13-1. Confirmation of Effect on Angiogenesis The degree of sprouting from the aortic ring caused by treatment with VEGF was investigated as follows in order to identify the effect of capsiate or dihydrocapsiate on VEGF-induced angiogenesis.

The aortic ring was prepared from the artery of Sprague Dawley rat (6-8 weeks old). The aortic ring was placed on a 48-well plate coated with 120 µL of Matrigel and 50 µL of Matrigel was further added. Then, 200 µL of a medium (human endothelial serum-free medium, Invitrogen, USA) containing capsiate or dihydrocapsiate and VEGF or a medium containing only VEGF was added. 6 days later, the cells were fixed, stained using Diff-Quick and subjected to evaluation (0 to 5 points) in a double blinded manner.

Figure 12:
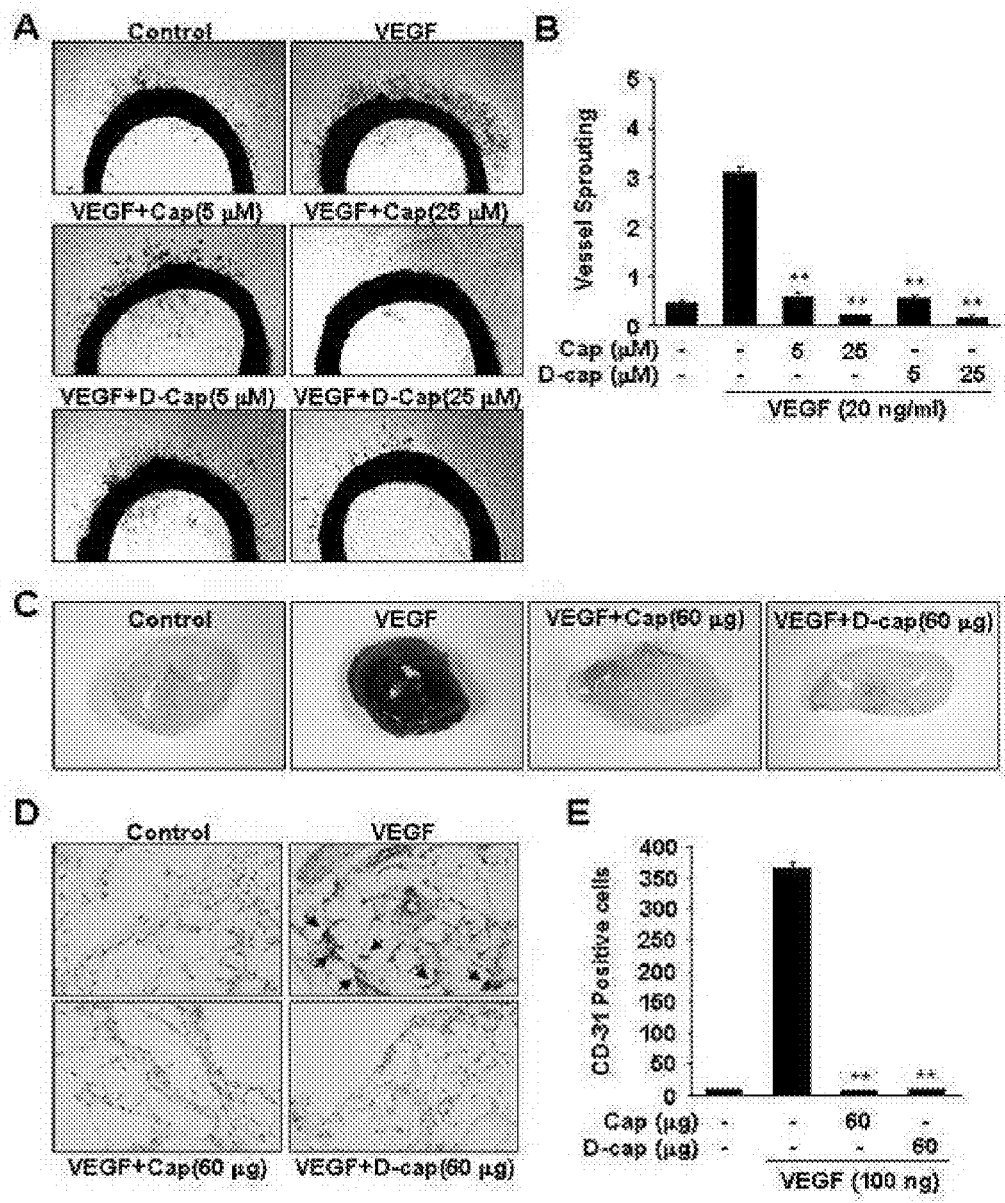
FIG. 12 shows the effect of capsiate and dihydrocapsiate on the sprouting (A, B) from the aortic ring, Matrigel plug (C) and the expression of endothelial cells (D, E) identified using and CD31.

As a result, as shown in FIGS. 12A and 12B, treatment with VEGF promoted sprouting from the aortic ring. However, treatment with capsiate or dihydrocapsiate inhibited the sprouting in concentration-dependent manner.

13-2. Confirmation of Effect on Angiogenesis

Mouse Matrigel plug was carried out in order to investigate the effect of capsiate or dihydrocapsiate on VEGF-induced angiogenesis in vivo [Min K J et al., 2007, *Blood*, 15: 1495-1502].

0.6 mL of Matrigel containing 60 µg of capsiate or dihydrocapsiate, 100 ng of VEGF and 10 units of heparin or Matrigel containing 100 ng VEGF only was administered to C57/BL6 mouse (Orient, Korea) through subcutaneous injection. 6 days later, the produced Matrigel plug was taken out.

As a result, as shown in FIG. 12C, the plug exhibited dark red color when only VEGF was contained, indicating that the blood vessels are rich in red blood cells, which, in turn, indicates that a lot of blood vessels were produced in the Matrigel due to VEGF-induced angiogenesis. In contrast, when capsiate or dihydrocapsiate was contained, the color was pale similarly to when only the Matrigel was administered, indicating that angiogenesis hardly occurred.

13-3. Measurement of Endothelial Cell Content

Immunohistochemical staining was carried out using CD31 in order to measure the endothelial cell content in the Matrigel plug.

The Matrigel plug was fixed using 2% formaldehyde and moisture was removed from the Matrigel using 15% sucrose and 30% sucrose based on the principle of osmosis. Then, the Matrigel plug was hardened at −70° C. The hardened Matrigel plug was sliced with a thickness of 8-12 µm, stained with CD31-antibody (PECAM-1 antibody, BD Biosciences, USA) and the level of expression by endothelial cells was observed under a microscope.

As a result, as shown in FIGS. 12D and 12E, a lot of endothelial cells expressed CD31 when they were treated with VEGF. However, when the cells were treated with capsiate or dihydrocapsiate, the level of CD31 expression decreased to the extent comparable to the control group.

Accordingly, it was confirmed in animal model that capsiate or dihydrocapsiate has the effect of inhibiting angiogenesis.

Example 14

Inhibition Effect of Capsiate on Proliferation and Activation of T Cells 14-1. Inhibition Effect of on Proliferation of T Cells T cells were isolated from mouse spleen in order to investigate the effect of capsiate on the proliferation of T cells. Specifically, the spleen of C57/BL6 mouse was taken out and pulverized as single cells. After lysing red blood cells using an RBC lysis buffer (Sigma, USA), other cells were washed 3 times using cell culture medium (RPMI 1640 complete medium). The cell culture medium is prepared by adding 10% FBS, 10 mM HEPES, 100 μg/mL penicillin, 100 μg/mL streptomycin, 2 mM L-glutamine, 1 mM sodium pyruvate and 50 uM 2-mercaptoethanol. From the cells, only the T cells were separated using a T cell enrichment column (R&D, USA).

$5 \times 10^5$ of the isolated T cells were placed on a 96-well plate and capsiate was treated at a concentration of 25 uM. Proliferation of T cells was induced by adding 0.1 μg/mL α-CD3a and 2 μg/mL α-CD28, or 1 μg/mL α-CD3a and 2 μg/mL α-CD28. The degree of cell proliferation was compared to that of the control group which was not treated with capsiate. Specifically, after culturing the T cells for 24 hours, thymidine (H3) was added at concentration of 1 uCi per well and the T cells were harvested 16 hours later using a membrane filter (Skatron, England) and a cell harvester. The harvested T cells were lysed in LSC cocktail solution (Ultima Gold, PerkinElmer, USA) and H3's CPM value was measured using a beta counter (Packard, USA). The result is given in FIG. 13.

Figure 13:
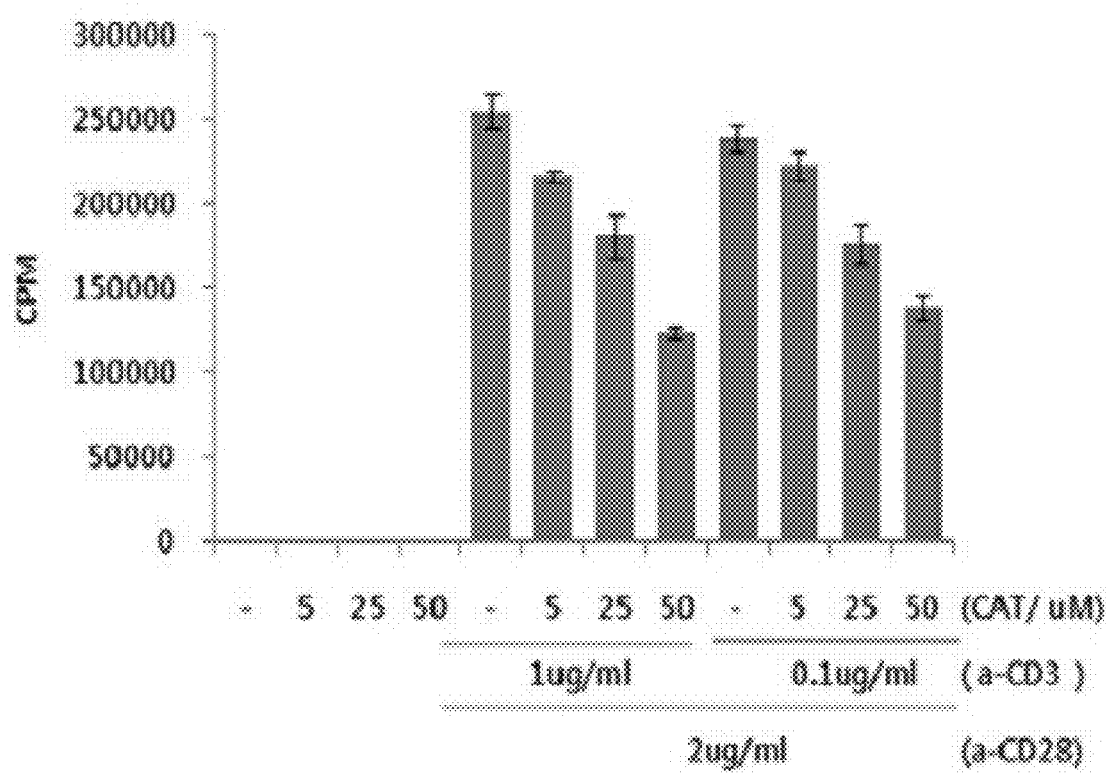
FIG. 13 shows the effect of capsiate on the proliferation of T cells.

As shown in FIG. 13, treatment with capsiate resulted in significant inhibition of the proliferation of T cells induced by α-CD3a and α-CD28, as compared to the control group.

14-2. Inhibition Effect on Secretion of IL-2 by T Cells

In order to investigate the effect of capsiate on activation of T cells, the production of IL-2 by the T cells the proliferation of which was induced in Example 14-1 was compared with the non-capsiate-treated control group. IL-2 is a T cell proliferation factor secreted from stimulated T cells and acts as a cytokine affecting the proliferation of T helper cells, cytotoxic T (TC) cells and natural killer (NK) cells, activation of T cells, proliferation of B cells, and production of antibody.

Specifically, the degree of IL-2 production was measured by ELISA. IL-2 recognition antibody was attached on a 96-well plate. Next day, after suppressing non-specific recognition using blocking buffer (PBS containing 5% BSA), cultured T cells were added to the plate and incubated at room temperature for 4 hours. Subsequently, after incubating using biotinylated IL-2 secondary antibody (Becton Dikinson, USA), absorbance (540 nm) was measured using an ELISA reader using biotin-recognizing enzyme antibody (streptavidine-conjugated HRP, Becton Dikinson, USA), while varying the substrate. Thus identified secretion of IL-2 production by T cells is given in FIG. 14.

Figure 14:
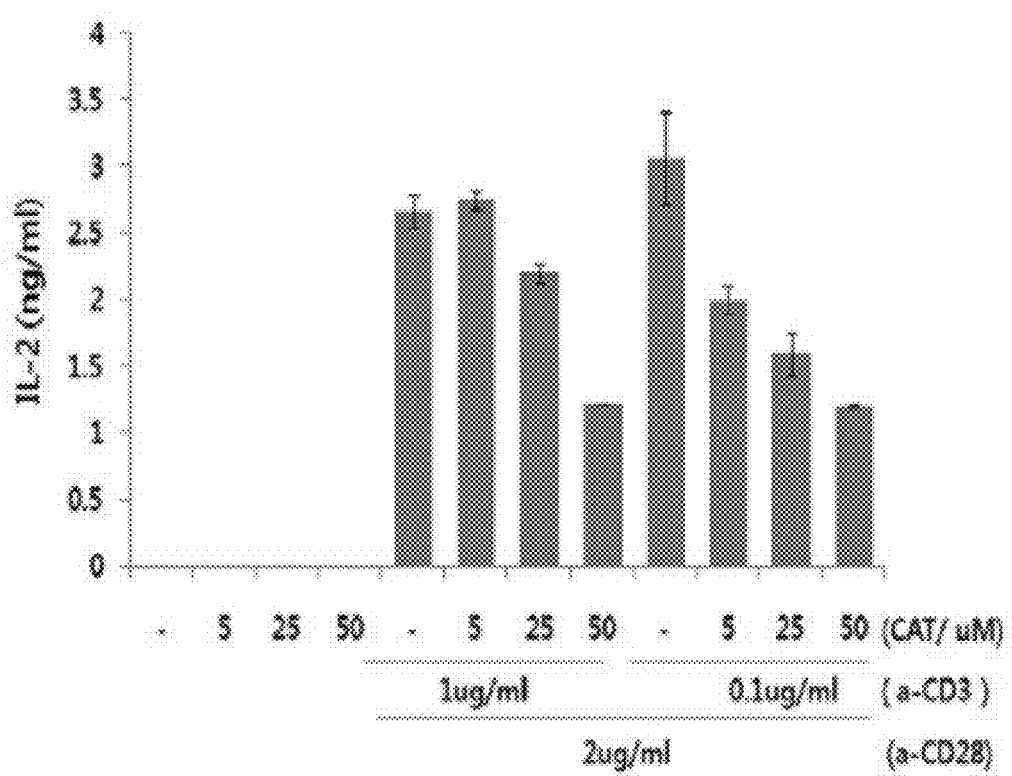
FIG. 14 shows that capsiate is effective in suppressing the secretion of IL-2 in T cells.

As shown in FIG. 14, treatment with capsiate resulted in significantly decreased IL-2 production by T cells, as compared to the control group. Accordingly, it was confirmed that capsiate can inhibit the activation of T cells.

14-3. Inhibition Effect on Tyrosine Phosphorylation in T Cells

Western blotting was carried out using anti-tyrosine phosphorylation (anti-PY) antibody in order to investigate the mechanism by which the proliferation of T cells is inhibited by capsiate.

Specifically, $5 \times 10^5$ of the T cells isolated in Example 14-1 was placed on a 96-well plate and capsiate was treated at concentrations of 5 and 25 uM. After treating with 2 μg/mL α-CD3 and α-CD4, or 2 μg/mL α-CD3, followed by incubation for 10 minutes in ice and then incubation for 10 minutes at 37° C., centrifuge was carried out. The cells obtained from the centrifuge was lysed using RIPA buffer containing 2 mM EDTA, 137 mM NaCl, 20 mM Tris-HCl (pH 8.0), 1 mM sodium vanadate, 10 mM NaF, 1 mM phenylmethanesulfonyl fluoride (PMSF), 1% NP-40, 10% glycerol and protease inhibitor cocktail, and subjected to SDS-PAGE electrophoresis using 10% acrylamide gel in order to isolate the proteins. The isolated proteins were transferred to a nylon membrane and tyrosine phosphorylated proteins were separated using mouse anti-PY antibody (Becton Dickison, USA) and anti-mouse IgG-HRP conjugation antibody (1; 10,000, Zymed) as the secondary antibody. The isolated proteins were detected by ECL (Amersham, USA) and visualized using RAS 3000 imaging system (Fuji Film, Japan). The result is given in FIG. 15.

Figure 15:
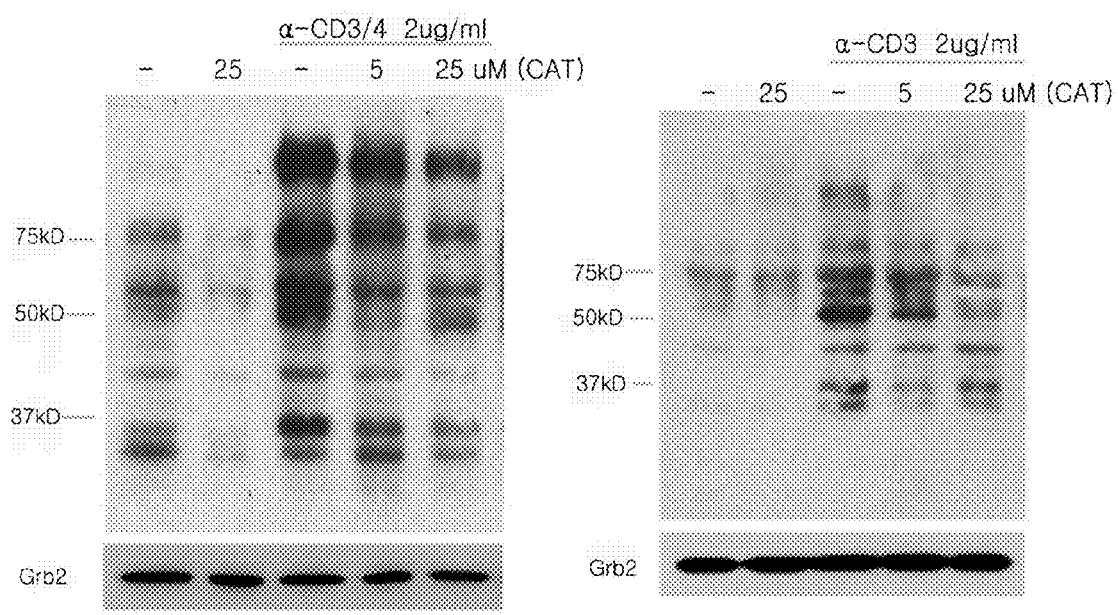
FIG. 15 shows that capsiate is effective in suppressing tyrosine phosphorylation in T cells.

As shown in FIG. 15, treatment with capsiate inhibited tyrosine phosphorylation in T cells, as compared to the control group. Especially, the tyrosine phosphorylated 56 kD protein in FIG. 15 is deemed as p-Lck. Considering that Lck is a tyrosine kinase which induces the tyrosine phosphorylation of CD4 and CD8 in T cells and greatly affects the activation of T cells, thereby inducing the T cell growth factor IL-2 [Boyman O et al., *Expert Opin. Biol. Ther.* 2006], it was confirmed that capsiate can inhibit the proliferation of T cells, as in Example 14-1, and the activation of T cells, as in Example 14-2, by inhibiting the phosphorylation of Lck.

INDUSTRIAL APPLICABILITY

As can be seen from the foregoing, the present invention provides a composition for preventing and treating inflammatory disease, angiogenesis-related disease and autoimmune disease or a immunosuppressant comprising capsiate, dihydrocapsiate or a pharmaceutically acceptable salt thereof as an effective ingredient. The composition and immunosuppressant of the present invention may be used for preventing and treating inflammatory disease, angiogenesis-related disease or autoimmune disease, or for suppressing immunity.

The invention claimed is:

1. A method for treating skin disease comprising administering a capsinoid compound represented by Chemical Formula 1 or Chemical Formula 2, or a pharmaceutically acceptable salt thereof as the only active ingredient to a subject in need thereof at an effective dose, wherein the skin disease is selected from the group consisting of acute/chronic eczema, urticaria, and psoriasis; and wherein Chemical Formula 1 is:

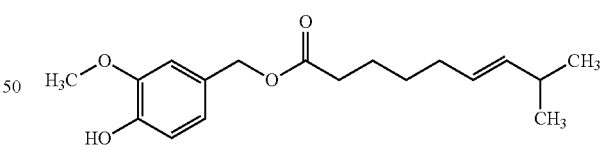

and Chemical Formula 2 is:

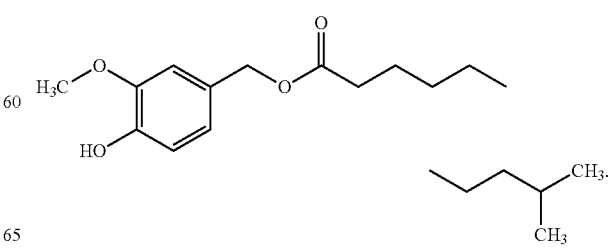

2. The method for treating skin disease of claim 1, wherein the skin disease is psoriasis.

3. The method for treating skin disease of claim 1, wherein the skin disease is acute/chronic eczema.

4. The method for treating skin disease of claim 1, wherein the skin disease is urticaria.

5. The method for treating skin disease of claim 1, wherein the capsinoid compound represented by Chemical Formula 1 or Chemical Formula 2 is an isolated capsinoid compound.

\* \* \* \* \*